(12) United States Patent
Tuller et al.

(10) Patent No.: US 7,194,891 B2
(45) Date of Patent: Mar. 27, 2007

(54) HIGH-TEMPERATURE GAS SENSORS

(75) Inventors: Harry L. Tuller, Wellesley, MA (US); Huankiat Seh, Boston, MA (US); Takeo Hyodo, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 21 days.

(21) Appl. No.: 10/828,096

(22) Filed: Apr. 20, 2004

(65) Prior Publication Data

US 2005/0229677 A1  Oct. 20, 2005

(51) Int. Cl.
*G01N 29/00* (2006.01)
*G01N 29/02* (2006.01)

(52) U.S. Cl. ............... 73/24.01; 73/24.06; 73/31.05; 73/579

(58) Field of Classification Search ............. 73/23.31, 73/24.01, 24.06, 31.05, 579
See application file for complete search history.

(56) References Cited

U.S. PATENT DOCUMENTS 3,991,360 A * 11/1976 Orth et al. ............... 324/468
5,151,110 A *  9/1992 Bein et al. ................ 95/140
6,370,955 B1    4/2002 Tuller et al.

(Continued)

FOREIGN PATENT DOCUMENTS

DE      199 31 007 A1   1/2001

(Continued)

OTHER PUBLICATIONS

Bund, A., et al., "Validation of the Frequency Shift of Thickness-Shear-Mode Resonators in Liquids—Determination of the Activation Energy of Viscosity," *Ber. Bunsenges. Phys. Chem.*, 101(12): 1960-1962 (1997).

(Continued)

*Primary Examiner*—Daniel S. Larkin
(74) *Attorney, Agent, or Firm*—Hamilton, Brook, Smith & Reynolds, P.C.

(57) ABSTRACT

A method of sensing the amount of a gas in a fluid flow includes operating an acoustic wave (AW) sensor at a first resonant frequency. The AW sensor includes a high temperature stable piezoelectric plate coupled to a first gas-absorbing layer. Also included is combining a fluid flow having a gas component with the first gas-absorbing layer at a temperature of at least about 500° C. At least one resonant frequency of the AW sensor is sensed. The amount of gas in the fluid flow is sensed by correlating the resonant frequency with the amount of gas absorbed in the first gas-absorbing layer.

A sensor for sensing the amount of a gas in a fluid flow includes a first gas-absorbing layer, a high-temperature-stable piezoelectric plate coupled to the first gas-absorbing layer, and a controller coupled to the high-temperature-stable piezoelectric plate. The controller is coupled to the high-temperature stable piezoelectric plate to measure a resonant frequency in the high temperature stable piezoelectric plate correlated with an amount of gas absorbed by the first gas absorbing layer, whereby the amount of a gas in a fluid flow is sensed. The high-temperature-stable piezoelectric plate is formed of at least one material selected from the group consisting of AlN, GaN, $Al_{1-x}Ga_xN$ ($0 \leq x \leq 1$), $GaPO_4$, $AlPO_4$, and materials having the crystal structure of $Ca_2Ga_2Ge_4SiO_{14}$, e.g., $Ca_2Ga_2Ge_4SiO_{14}$, $La_3Ga_5SiO_{14}$, $La_3Ga_{5.5}Nb_{0.5}O_{14}$, $La_3Ga_{5.5}Ta_{0.5}O_{14}$, and the like.

58 Claims, 11 Drawing Sheets

U.S. PATENT DOCUMENTS

2003/0115860 A1 6/2003 May et al.
2005/0226773 A1* 10/2005 Liu ........................ 422/68.1

FOREIGN PATENT DOCUMENTS

JP 3-264856 A * 11/1991
WO WO 96/31773 10/1996

OTHER PUBLICATIONS

Fritze, H., et al., "High Temperature Bulk Acoustic Wave Properties of Langasite," *Phys. Chem. Chem. Phys.*, 5(23): 5207-5214 (2003).

Fritze, H., et al., "Thin Film Stoichiometry Determination by High Temperature Microbalance Technique," *Mat. Res. Soc. Symp.Proc.*, 756: 181-186 (2003).

Kim, Yong-Wha et al., "Phenomenological Control Oriented Lean $NO_x$ Trap Model," *SAE Technical Paper Series* (2003-01-1164) (2003).

Sasahara, K., et al., "Macroporous and Nanosized Ceramic Films Prepared by Modified Sol-Gel Method with PMMA Microsphere Templates," *J. Euro. Ceramic Soc.*, 24, 1961-1967 (2004).

Fritze, H., et al., "High Temperature Nanobalance Sensor Based on Langasite," *Sensors and Actuators*, B 76: 103-107 (2001).

Fritze, H., et al., "Operational Limits of Langasite High Temperature Nanobalances," *J. Euro. Ceramic Soc.*, 21: 1473-1477 (2001).

Fritze, H., et al., "Langasite for High Temperature Bulk Acoustic Wave Applications," *App. Phys. Lett.*, 78(7): 976-977 (2001).

Moos, Ralf, et al., "Selective Ammonia Exhaust Gas Sensor for Automotive Applications," *Sensors and Actuators*, B 83: 181-189 (2002).

Smith, Warren L., et al., "Precision Oscillators." In *Precision Frequency Control*, E. A. Gerber et al., eds. (FL: Academic Press Inc.), pp. 45-98 (1985).

Thiele, J. A., et al., "High Temperature LGS SAW Devices with $Pt/WO_3$ and Pd sensing films," *Dept. Of Electrical and Computer Engineering, University of Maine*, Orono, ME., USA, *IEEE Ultrasonics Symposium Proceedings*, 1: 1750-1753 (2003).

Tamaki, J., et al., "Application of metal tungstate-carbonate composite to nitrogen oxides sensor operative at elevated temperatur," *Sensors and Actuators B Chemical*, 25(1-3): 396-399 (1995).

* cited by examiner

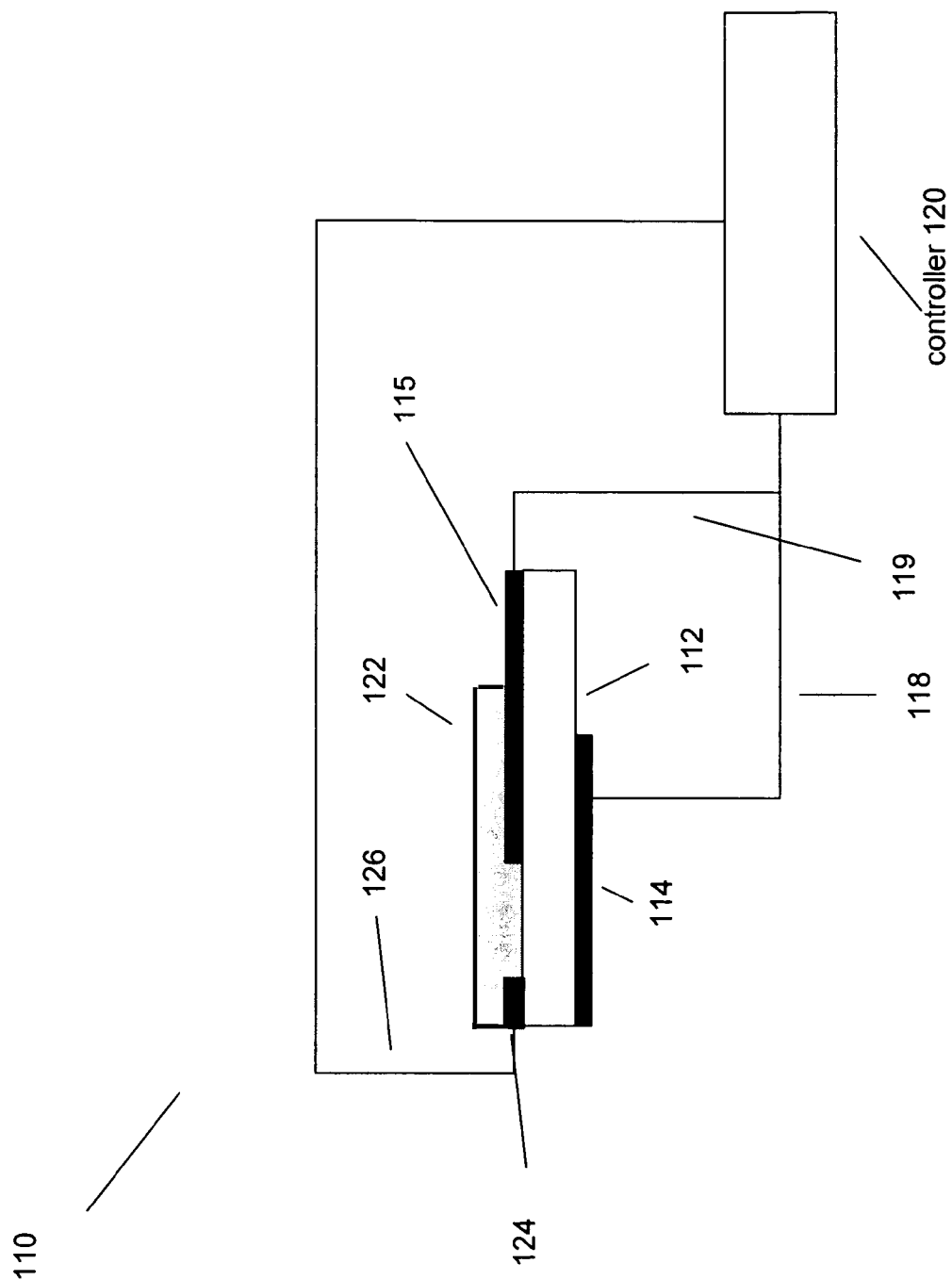

HIGH-TEMPERATURE GAS SENSORS

GOVERNMENT SUPPORT

This invention was made with government support under Grant Number DMR-0228787 awarded by NSF. The Government has certain rights in the invention.

BACKGROUND OF THE INVENTION

Numerous high-temperature fluid flow processes exist where it is desirable to measure the amount (e.g., concentration or rate of change of concentration versus time) of various species, e.g., gas species. Particular applications include chemical reaction processes, typically gaseous processes, e.g., pyrolysis or cracking of hydrocarbons, e.g., from petroleum or other chemical feedstocks. Other applications include gas flows in combustion process, e.g., external combustion, e.g., furnaces, boilers, burners, and the like; internal combustion engines, e.g., four stroke engines, two stroke engines, diesel engines, and the like, and turbine engines, e.g., jet engines, gas turbines, and the like.

For example, high-temperature capable $NO_x$ sensors are required to measure $NO_x$ emissions from road vehicles, off-road vehicles (e.g., construction equipment), and power generating equipment. $NO_x$, which can include one or both of NO and $NO_2$, plays an important role in atmospheric reactions that cause harmful particulate matter, ground level ozone and other smog-forming pollutants, and acid rain, and is the focus of legislation in the US and Europe that focuses on large decreases in $NO_x$ emission levels. Robust $NO_x$ sensors are much in demand in the industry.

Many techniques exist for sensing such gases, for example, mass spectrometry, hot wire detectors, optical spectroscopy, adsorption onto coated microbalances, and others. However, these techniques are not readily applicable for all applications, for example, mass spectrometry can be too complex and fragile for large scale measuring of gases in internal combustion engines, optical spectroscopy can be obscured by particulates produced in combustion processes, and adsorption onto coated microbalances is incompatible with high temperatures and high variations in gas concentration.

SUMMARY OF THE INVENTION

Disclosed herein are methods, sensors, and systems for measuring amounts of gas in fluid flows at high temperature.

A method of sensing the amount of a gas in a fluid flow includes operating an acoustic wave (AW) sensor at a first resonant frequency. The AW sensor includes a high temperature stable piezoelectric plate coupled to a first gas-absorbing layer. Also included is combining a fluid flow having a gas component with the first gas-absorbing layer at a temperature of at least about 500° C. At least one resonant frequency of the AW sensor is sensed. The amount of gas in the fluid flow is sensed by correlating the resonant frequency with the amount of gas absorbed in the first gas-absorbing layer.

A sensor for sensing the amount of a gas in a fluid flow includes a first gas-absorbing layer, a high-temperature-stable piezoelectric plate coupled to the first gas-absorbing layer, and a controller coupled to the high-temperature-stable piezoelectric plate. The controller is coupled to the high-temperature stable piezoelectric plate to measure a resonant frequency in the high temperature stable piezoelectric plate correlated with an amount of gas absorbed by the first gas absorbing layer, whereby the amount of a gas in a fluid flow is sensed. The high-temperature-stable piezoelectric plate is formed of at least one material selected from the group consisting of AlN, GaN, $Al_{1-x}Ga_xN$ ($0 \leq x \leq 1$), $GaPO_4$, $AlPO_4$, and materials having the crystal structure of $Ca_2Ga_2Ge_4SiO_{14}$, e.g., $Ca_2Ga_2Ge_4SiO_{14}$, $La_3Ga_5SiO_{14}$, $La_3Ga_{5.5}Nb_{0.5}O_{14}$, $La_3Ga_{5.5}Ta_{0.5}O_{14}$, and the like.

A method of sensing the amount of a gas component in a fluid flow includes: operating an acoustic wave (AW) sensor at a first resonant frequency, the AW sensor including a piezoelectric plate coupled to a first gas-absorbing layer, the gas absorbing layer comprising a metal carbonate; combining a fluid flow having a gas component with the first gas-absorbing layer; and sensing at least one resonant frequency of the AW sensor, whereby the resonant frequency can be correlated with the amount of gas absorbed in the first gas-absorbing layer, thereby sensing the amount of gas in the fluid flow. In some embodiments of the invention, the piezoelectric plate is formed of one or more materials selected from the group consisting of AlN, GaN, $Al_{1-x}Ga_xN$ ($0 \leq x \leq 1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$.

An acoustic wave (AW) sensor for sensing the amount of a gas in a fluid flow includes a first gas-absorbing layer comprising a metal carbonate; a piezoelectric plate coupled to the first gas-absorbing layer; and a controller coupled to the piezoelectric plate to measure a resonant frequency piezoelectric plate correlated with an amount of gas absorbed by the first gas absorbing layer, whereby the amount of a gas in a fluid flow is sensed. In some embodiments of the invention, the piezoelectric plate is formed of one or more materials selected from the group consisting of AlN, GaN, $Al_{1-x}Ga_xN$ ($0 \leq x \leq 1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$.

This invention offers several advantages both over the use of conventional piezoelectric balances and over the use of known methods for measuring amounts of gas in fluid flows at high temperatures.

For example, the use of a high-temperature piezoelectric balance allows for in situ measurement gases at high temperatures. The piezoelectric materials provided in various embodiments of the invention are stable over a much greater temperature range than that of more-conventional piezoelectric materials, such as quartz. Consequently, these materials can be used to accurately measure changes in amounts of gas in fluid flows at high temperature, for example, various embodiments of the invention can be employed to reliably and accurately measure gas components, e.g., $NO_x$, in the exhaust stream of an internal combustion engine where the temperature is at least about 500° C.

The use of a gas absorbing layer can allow for specific absorption of a particular gas over other gases. Also, the gas absorbing layer can absorb a much greater amount of gas compared to a gas adsorption layer, whereby a wider range of gas concentrations can be reliably measured. Additionally, in some embodiments of the invention, gas amounts correlated to frequency measurements and electrical complex impedance measurements can be compared. The preceding features can lead to improved sensor sensitivity or signal-to-noise ratios.

Thus, in various embodiments of the invention, sensing of gas at high temperatures is provided that enables, for example, $NO_x$ detection in the exhaust stream of an internal combustion engine, in one example in combination with a Lean $NO_x$ Trap (LNT). A Lean $NO_x$ Trap (LNT), functions by preoxidizing NO in $NO_x$ to $NO_2$ and storing the $NO_x$ in the trap. When the trap is saturated, the stored $NO_x$ ($NO_2$) is purged by switching the engine to rich burn operation, thereby reducing the $NO_x$ to $N_2$. It is desirable for efficient engine operation to limit rich burn operation to the time necessary to purge the trap. The $NO_x$ sensor of the invention can provide the high temperature $NO_x$ sensing necessary for the LNT system to efficiently control $NO_x$ emissions in an internal combustion engine.

In another embodiment of the invention, ammonia is sensed in the exhaust of an internal combustion engine (e.g., a diesel engine), for example, in combination with a selective catalytic reduction (SCR) system for reducing $NO_x$ with ammonia to $N_2$. The SCR system can be employed in diesel engines to reduce $NO_x$ to $N_2$. The high temperature ammonia sensor of the invention can provide the necessary feedback to an ammonia dosing unit (which typically injects urea as an ammonia precursor) so that sufficient ammonia is introduced to reduce the $NO_x$ without allowing excess ammonia to be released into the atmosphere. This can result in more efficient operation of the engine and minimize toxic ammonia emissions.

These and other advantages will be more apparent from the following description.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 depicts an embodiment of an acoustic wave (AW) sensor 110 employed in the method of the invention, which includes a high temperature stable piezoelectric plate 112, coupled to a gas absorbing layer 122 and electrically coupled to controller 120.

FIG. 2A depicts sensor 110 operating in conjunction with a gas trap 212 (e.g., a Lean $NO_x$ Trap (LNT)), wherein sensor 110 is located in series downstream of trap 212 with respect to the flow direction of fluid flow 210.

FIG. 2B depicts sensor 110 in parallel with trap 212 with respect to the direction of fluid flow 210.

FIG. 2C depicts sensor 110 in series upstream of trap 212 with respect to the direction of fluid flow 210.

DETAILED DESCRIPTION OF THE INVENTION

Figure 2A:
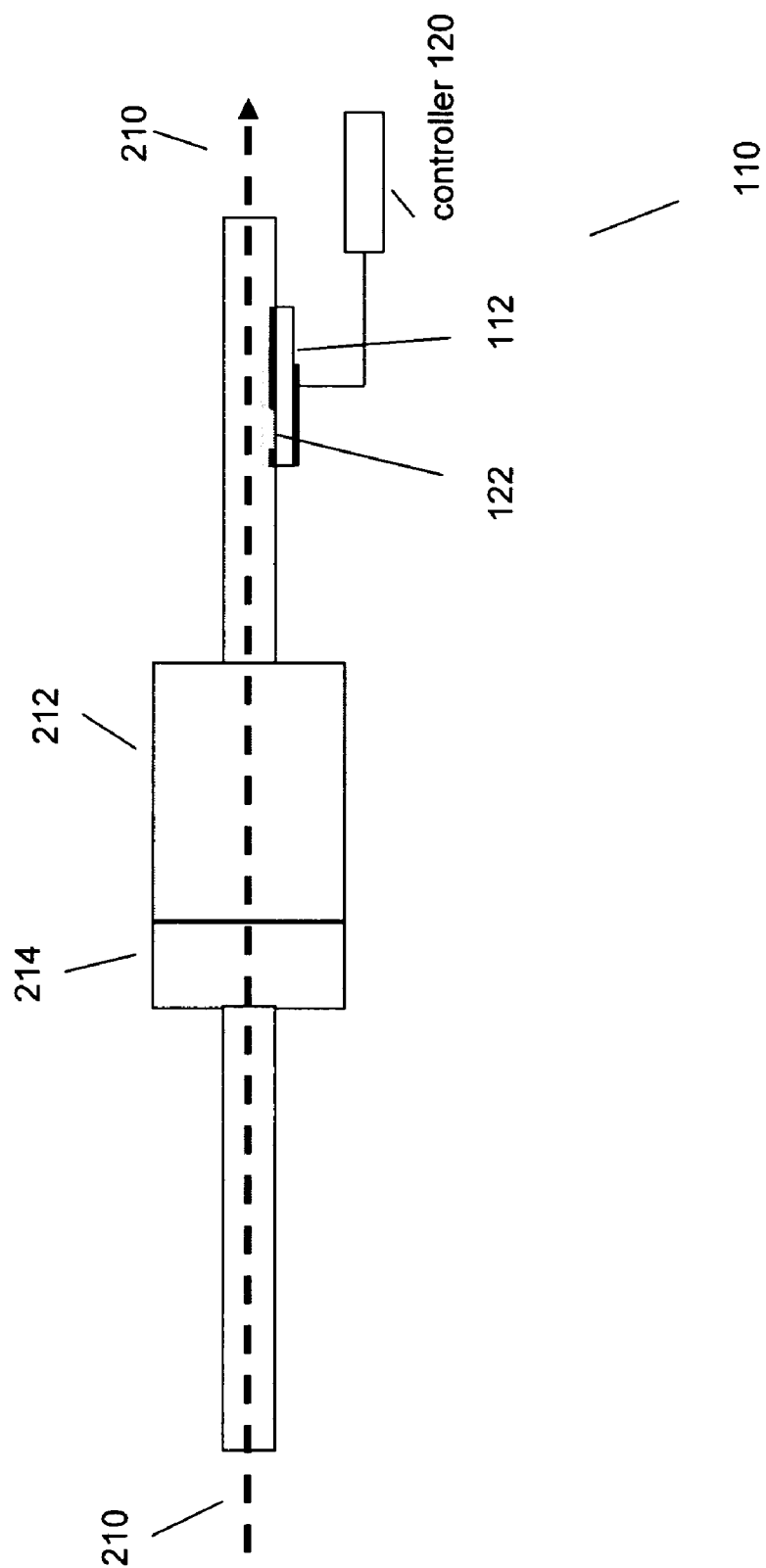
FIGS. 2A, 2B, and 2C depict embodiments of the invention wherein AW sensor 110 is brought into contact with a fluid flow 210, e.g., an exhaust stream from an internal combustion engine, whereby the amount of a gas component in the fluid flow can be measured by one embodiment of the method of the invention.

A description of preferred embodiments of the invention follows.

FIG. 1 shows an acoustic wave (AW) sensor 110 which includes high temperature stable piezoelectric plate 112 contacted by electrodes 114/115. As shown, electrodes 114/115 are contacted to opposite surfaces of high temperature stable piezoelectric plate 112. Leads 118/119 join electrodes 114/115 with controller 120. Gas absorbing layer 122 is coupled to the surface of high temperature stable piezoelectric plate 112. In other embodiments of the invention, electrodes 114/115 can contact the AW sensor in other arrangements which can be apparent to one of ordinary skill in the art. In some embodiments of the invention, optional electrode 124 and lead 126 along with electrode 115 and lead 119 couple controller 120 to gas absorbing layer 122, whereby electrical characteristics of layer 122 that can be correlated to resonant frequency, e.g., electrical complex impedance, can be measured.

To measure a resonant frequency in sensor 110, controller 120 has an impedance function which can apply an alternating voltage across the electrodes 114/115, causing atoms within the crystalline structure of the piezoelectric material to vibrate. Controller 120 can also measure the electrical admittance of the piezoelectric material as a function of frequency. In some embodiments of the invention, a separate voltage source can be used to provide the alternating voltage.

The amplitude of the admittance signal provides an indication of the amplitude of vibration within the piezoelectric material. At any given temperature, the amplitude of vibration varies as a function of the frequency of the voltage source. The frequency at which the admittance is greatest is the "resonance frequency." At the resonance frequency, the atoms of the piezoelectric material oscillate with maximum amplitude. Conversely, the frequency of minimum admittance (and, consequently, minimum vibration amplitude) is known as the "antiresonance frequency."

The resonance frequency of the AW sensor can be, in part, a function of the dimensions of the balance. In preferred embodiments of the invention, the dimensions of the piezoelectric balance are selected to produce a resonance frequency of about 10 MHZ. Typically, the electrodes 114/115 are key-hole shaped and formed of platinum.

Controller 120 can measure impedance in a "passive" method for measuring frequency shift. Alternatively, an "active" method can be used to measure frequency shift. The active method, which is usually performed in commercial devices, uses the resonator as the frequency-determining device in an electronic feedback circuit. The passive method, typically employed with the apparatus of FIG. 1, can yield more detailed information, such as the real and imaginary parts of the impedance. Additional discussion of the active method and a comparison of the active and passive methods is provided in Precision Frequency Control, Vol. 2, Chapter 8: "Bulk-Acoustic-Wave Oscillators" 47 (1985) and in A. Bund. et al., "Validation of the Frequency Shift of Thickness-Shear-Mode Resonators in Liquids—Determination of the Activation Energy of Viscosity," 101 Ber. Bunsenges. Phys. Chem. (No. 12) 1960–62 (1997), the teachings of both references are incorporated herein by reference in their entireties.

As gas is absorbed or desorbed from gas absorbing layer 122, the resonance or antiresonance frequency of sensor 110 can be measured. These measurements can be taken at a fixed temperature or as sensor 110 (and, e.g., the system wherein it can be sensing gas, e.g., an exhaust stream of an internal combustion engine) experiences changing temperatures. As gas is absorbed, the resonance and antiresonance frequencies of sensor 110 can decrease. Conversely, as gas desorbs from sensor 110, the resonance and antiresonance frequencies can increase. Where high temperature stable piezoelectric plate 112 includes langasite ($La_3Ga_5SiO_{14}$), the antiresonance frequency (rather than the resonance frequency) typically is used as the characteristic frequency because of the steeper slope at zero crossing of the imaginary part of the impedance in comparison to that of the resonance frequency. The resultant change in amount of gas sensed can then be measured as a function of the change in anti-resonance or resonance frequency.

In some embodiments of the invention, when electrode 124 and lead 126 couple controller 120 to gas absorbing layer 122, controller 120 has a second impedance function which can apply an alternating voltage over some frequency range across the electrode 124 and electrode 115, which can cause charge carriers within gas-absorbing layer 122 to periodically displace, whereby electrical characteristics correlated with the resonant frequency of layer 122, e.g., complex electrical impedance, can be measured. This value can be correlated with the amount of gas absorbed by layer 122, for example, in some embodiments of the invention wherein layer 122 includes a zeolite, thereby sensing the amount of gas in the fluid flow. In other embodiments of the invention, both gas measurement modes can be compared, e.g., the amount of gas sensed by the impedance of layer 122 and the amount of gas sensed by the resonant frequency of sensor 110 can be compared. This can, for example, provide backup measurement in case of failure of one measurement mode, allow an improvement in signal to noise ratios, allow for error correction, e.g., correction of temperature-related drift in one measurement mode, and the like. For example, by employing both measurement modes, it can be possible to have temperature correction in a single sensor without having to employ a second AW sensor that is held at the same temperature but is not allowed to absorb gas.

In each of the various embodiments herein, methods and apparatus for temperature compensation are generally employed. For example, in some embodiments of the invention, a second sensor can be employed at the same temperature as AW sensor 110, except that the second sensor is not allowed to absorb gas; the second sensor can either be physically barred from contacting the gas component or the second sensor can lack the gas absorbing layer. Because they are at the same temperature, the difference in resonant frequency between AW sensor 110 and the second sensor can be correlated to the amount of gas absorbed on AW sensor 110, independent of temperature variations, thereby correcting for temperature variations. See, for example, Tuller, et al., U.S. Pat. No. 6,370,955; Tuller, H L and Fritze, H, "Langasite for high temperature bulk acoustic wave applications," *App. Phys. Lett.*, 78, (2001), 976–977; Tuller, et al., "High temperature nanobalance sensor based on langasite,", *Sensors and Actuators, B* 76, (2001), 103–107; Tuller, et al., "Operational limits of langasite high temperature nanobalances,", *J. Euro. Ceramic Soc.*, 21, (2001), 1473–1477. The entire teachings of these references are included herein by reference.

In other embodiments of the invention, a plurality of harmonics of the resonant frequency of AW sensor 110 are measured, for example, the first and third harmonics. Because different harmonics can respond differently to temperature variations, calibration experiments can be performed to measure the dependecy of each harmonic to temperature variations, whereby measurements of different harmonics during gas absorption can be compared to the calibration experiments and thereby compensated for temperature variations. See, for example, Fritze, H; Seh, H; Schneider, O; Tuller, H L; Borchardt, G; "Thin Film Stoichiometry Determination by High Temperature Microbalance Technique", *Materials Research Society Symposium—Proceedings*, v 756, 181–186 (2003); and Fritze, H; Schneider, O; Seh, H; Tuller, H L; Borchardt, G; "High temperature bulk acoustic wave properties of langasite" *Physical Chemistry and Chemical Physics* 5, 5207–5214 (2003). The entire teachings of the preceding references are included herein by reference.

In some embodiments of the invention, temperature correction can be provided by comparing the amount of gas sensed by the impedance of layer 122 and the amount of gas sensed by the resonant frequency of sensor 110, e.g., when electrode 124 and lead 126 couple controller 120 to gas absorbing layer 122, and controller 120 has a second impedance function which can apply an alternating voltage over some frequency range across the electrode 124 and electrode 115, which can cause charge carriers within gas-absorbing layer 122 to periodically displace, whereby electrical characteristics correlated with the resonant frequency of layer 122, e.g., complex electrical impedance, can be measured. For example, by employing both measurement modes, it can be possible to have temperature variation can be compensated for in a single sensor without having to employ a second AW sensor that is held at the same temperature but is not allowed to absorb gas. The different temperature dependencies of the resonant frequency of piezoelectric plate 112 and the electrical complex impedance of gas absorbing layer 122 can each be measured in calibration experiments, and the different temperature dependencies can be employed to compensate further resonant frequency or electrical complex impedance measurements for temperature variations.

Suitable high temperature piezoelectric materials, e.g., for high temperature stable piezoelectric plate 112, include bulk single-crystal forms of piezoelectric materials that remain stable and sufficiently resistive at elevated temperatures to resonate in response to the controller, particularly at temperatures above 500° C. Suitably stable piezoelectric materials preferably are those that have only a single solid phase so as to prevent destructive changes in the crystalline structure with change in temperature. As an alternative to the use of a single crystal, multiple single-crystal films or textured polycrystalline films of a suitable piezoelectric material can be grown and stacked to form a layered structure. Typically, the piezoelectric material can be non-reactive in the environments in which it operates and should not lose or gain its chemical constituents, e.g., oxygen gain or loss from $La_3Ga_5SiO_{14}$, at high temperatures.

Suitable high temperature piezoelectric materials can include, for example, materials of the $Ca_2Ga_2Ge_4SiO_{14}$—crystal structure-type (e.g., having the structure and optionally different chemical formula); (2) phosphates such as $GaPO_4$ and $AlPO_4$, or in some embodiments of the invention $AlPO_4$; and in other embodiments of the invention, $GaPO_4$; and (3) materials in the $Al_{1-x}Ga_xN$ ($0 \leq x \leq 1$) system, e.g., AlN, GaN, and $Al_{1-x}Ga_xN$ species where x has a value between, but not including 1; in some embodiments of the invention, species of $Al_{1-x}Ga_xN$ are employed where ($0 < x \leq 1$).

Specific members of the $Ca_2Ga_2Ge_4SiO_{14}$-crystal structure-type that are suitable for high temperature use with this invention include langasite ($La_3Ga_5SiO_{14}$), $La_3Ga_{5.5}Nb_{0.5}O_{14}$, and $La_3Ga_{5.5}Ta_5O_{14}$. In some embodiments of the invention, langasite is employed because it typically will not undergo any phase transformations up to its melting point at about 1470° C. Further, as is, langasite may be excited to exhibit bulk oscillations up to 750° C. and higher. Use of pure langasite can generally be limited by conductive losses, for example, at particularly high temperatures, the conductivity of pure langasite can rise to a level at which the langasite can no longer effectively resonate when a voltage is applied. Such conductive losses in the langasite can be compensated for by adding dopants that can increase the resistivity of the langasite and thereby enable its use at still higher temperatures.

Thus, in various embodiments of the invention, the high-temperature piezoelectric material for plate 112 is formed of at least one material selected from the group consisting of AlN, GaN, $Al_{1-x}Ga_xN$ ($0 \leq x \leq 1$), $GaPO_4$, $AlPO_4$, and materials having the crystal structure of $Ca_2Ga_2Ge_4SiO_{14}$, e.g., $Ca_2Ga_2Ge_4SiO_{14}$, $La_3Ga_5SiO_{14}$, $La_3Ga_{5.5}Nb_{0.5}O_{14}$, $La_3Ga_{5.5}Ta_{0.5}O_{14}$, and the like, or more typically, at least one material selected from the group consisting of AlN, $Al_{1-x}Ga_xN$ ($0 < x \leq 1$), $AlPO_4$, $Ca_2Ga_2Ge_4SiO_{14}$, $La_3Ga_5SiO_{14}$, $La_3Ga_{5.5}Nb_{0.5}O_{14}$, and $La_3Ga_{5.5}Ta_{0.5}O_{14}$.

In other embodiments of the invention, the high-temperature piezoelectric material for plate 112 is formed of at least one material selected from the group consisting of GaN, $Al_{1-x}Ga_xN$ ($0 < x \leq 1$), $GaPO_4$, $AlPO_4$, and materials having the crystal structure of $Ca_2Ga_2Ge_4SiO_{14}$; in some embodiments, at least one material selected from the group consisting of $GaPO_4$ and $AlPO_4$; in other embodiments, at least one material selected from the group consisting of GaN, $Al_{1-x}Ga_xN$ ($0 < x \leq 1$), and materials having the crystal structure of $Ca_2Ga_2Ge_4SiO_{14}$; and in other embodiments, at least one material selected from the group consisting of materials having the crystal structure of $Ca_2Ga_2Ge_4SiO_{14}$. In some embodiments of the invention, the high-temperature piezoelectric material for plate 112 is formed of at least one material selected from the group consisting of $Ca_2Ga_2Ge_4SiO_{14}$, $La_3Ga_5SiO_{14}$, $La_3Ga_{55}Nb_{05}O_{14}$, and $La_3Ga_{5.5}Ta_{0.5}O_{14}$. In some embodiments of the invention, the high-temperature piezoelectric material for plate 112 is $La_3Ga_5SiO_{14}$.

Thus, in some embodiments of the invention, the high-temperature-stable piezoelectric plate is stable as a single crystalline phase in an oxygen partial pressure range between about 5 atmospheres (atm) to about $10^{-22}$ atm and a temperature range between about −40° C. to 900° C. In other embodiments of the invention, the high-temperature-stable piezoelectric plate is stable as a single crystalline phase in temperature range between about −30° C. to about 650° C.

In contrast to the use of conventional piezoelectric materials in room-temperature applications, the high-temperature piezoelectric sensors of the present embodiments of the invention have a bulk resistivity, $R_p$, at high temperature that typically can not be neglected because $R_p$ can become sufficiently small at elevated temperatures to attenuate the resonance signal. Consequently, methods and circuits for correcting for the effects of high temperature on $R_p$ have been developed, which can be employed with any of the present embodiments of the invention; see, for example, Tuller, et al., U.S. Pat. No. 6,370,955, the entire teachings of which are incorporated herein by reference.

Gas-absorbing layer 122 is a thick film of a material that preferentially absorbs a gas. In the gas-absorbing layer, under conditions suitable for absorption of the gas by the layer, the gas in contact with the layer is substantially absorbed within the layer compared to the amount adsorbed on the surface of the layer. As used herein, to "absorb" means to encompass molecules (for example ammonia, $NO_x$, and the like) within the physical boundaries of a solid, e.g., the gas absorbing layer. As used herein, "adsorbed" molecules are those contacting the exterior physical surface of a solid, e.g., if the solid is a cube, adsorbed gas consists of those gas molecules contacting the faces of the cube. Generally, the ratio of the amount of gas that is absorbed in versus adsorbed on the layer is about 100:1, typically about 500:1, and preferably about 2000:1. A "thick film", e.g., the gas absorbing layer, is a film that has sufficient interior volume compared to surface area exposed to a gas to make the preceding gas absorption/adsorption ratios possible. Thus, the gas-absorbing layers of the present embodiments of the invention are distinct from gas adsorbing layers, e.g., thin-films of semiconducting oxide that adsorb gas, and the like. Generally, a thick film has a surface area to volume ratio of less than about $10^6$ $cm^2$:1 $cm^3$, typically less than about $5 \times 10^6$ $cm^2$:1 $cm^3$, and preferably less than about $1 \times 10^7$ $cm^2$:1 $cm^3$.

A gas that is absorbed by an absorbing layer can form a chemical bond with the layer, e.g., forming a covalent or ionic bond, e.g., $NO_x$ gas can react with barium carbonate to form barium nitrate, $SO_x$ gas can react with barium carbonate to form barium sulfate, and the like. A gas that is absorbed by an absorbing layer can also be contained in the layer by non-covalent interactions, e.g., contained within nanopores, e.g., ammonia can be contained in the nanopores (e.g., from about 0.1 nm to about 10 nm in diameter) of a zeolite gas absorbing layer.

Thus, the gas absorbing layer can comprise any material that is absorbent for a gas and is thermally stable under suitable conditions, e.g., in some embodiments of the invention, first gas-absorbing layer includes one or more materials selected from the group consisting of metal carbonates and zeolites.

For example, suitable materials for acidic gases, e.g., $NO_x$ and $SO_x$, e.g., NO, $NO_2$, $SO_2$, $SO_3$, and the like, can include metal carbonates, e.g., carbonates of lithium, sodium, potassium, rubidium, cesium, beryllium, magnesium, calcium, strontium, barium, and other metal carbonates known to the art. In some embodiments of the invention, the layer employed for absorbing $NO_x$ is barium carbonate. In various embodiments of the invention, the materials described in this paragraph can be formed as microporous layers (distinct from the nanopores in, for example, zeolites), for example, a gas absorbing layer can have a microstructure, e.g., a regular microstructure of micropores having an average diameter from about 200 nm to about 3000 nm, typically from about 200 nm to about 1000 nm, or more typically, between about 400 nm and about 800 nm; see Example 1.

Gas absorbing layers, typically gas absorbing layers that reactively absorb gases, e.g., layers that include metal carbonates, can optionally include catalysts, e.g., metals, metal oxides, metal complexes, and the like, e.g., platinum, palladium, ruthenium, and the like. For example, barium carbonate layers can include platinum catalyst. See, for example, Kim, Y W; Sun, J; Kolmanovsky, I; Koncsol, J A; "Phenomenological control oriented lean $NO_x$ trap model". *SAE Technical Paper Series* (2003-01-1164) (2003), the entire teachings of which are incorporated herein by reference.

In other embodiments of the invention, suitable materials for absorbing any gas of interest include zeolites with pore sizes appropriate for absorption of the gas of interest. As used herein, "zeolites" include zeolites and zeolite-like crystalline solids, typically aluminosilicates, with well-defined nanopore (distinct from micropores in the preceding paragraph) structures, e.g., multi-dimensional interconnected channel structures with narrowly distributed nanopore size that ranges from about 0.1 nm (nanometer) to about 10 nm. In some embodiments of the invention, wherein first gas-absorbing layer 122 includes a zeolite, the zeolite can be, for example, selected from Linde Type A, zeolite beta, NaX, NaA, NaY, ZSM-5, H-ZSM-5, natrolite, chabazite, sodalite, faujasite, mordenite, MCM-41, MCM-48, and MCM-50. Suitable nanopore sizes can be determined by one of ordinary skill in the art based on the gas to be absorbed, for example, in some embodiments of the invention, nanopore sizes of between about 0.5 nm and about 0.6 nm are employed for absorption of ammonia. Suitable materials for other gases can include nanoporous materials, e.g., zeolites, that have nanopore sizes suitable for absorbing the desired gas or gases.

Typically, with respect to the other sensor materials it contacts (e.g., high temperature stable piezoelectric plate 112, electrodes 114/115, etc) the gas adsorbing layer can be chemically compatible or can be made to be chemically compatible. For example, in some embodiments of the invention, chemically compatible layers are by their chemical nature stable against chemical reaction, chemical species migration, or other thermochemical aging or degradation processes. In other embodiments of the invention, passivation or diffusion layers or barriers can be formed in-situ or applied during fabrication of the sensor to lie between layers which can otherwise react.

Figure 2B:
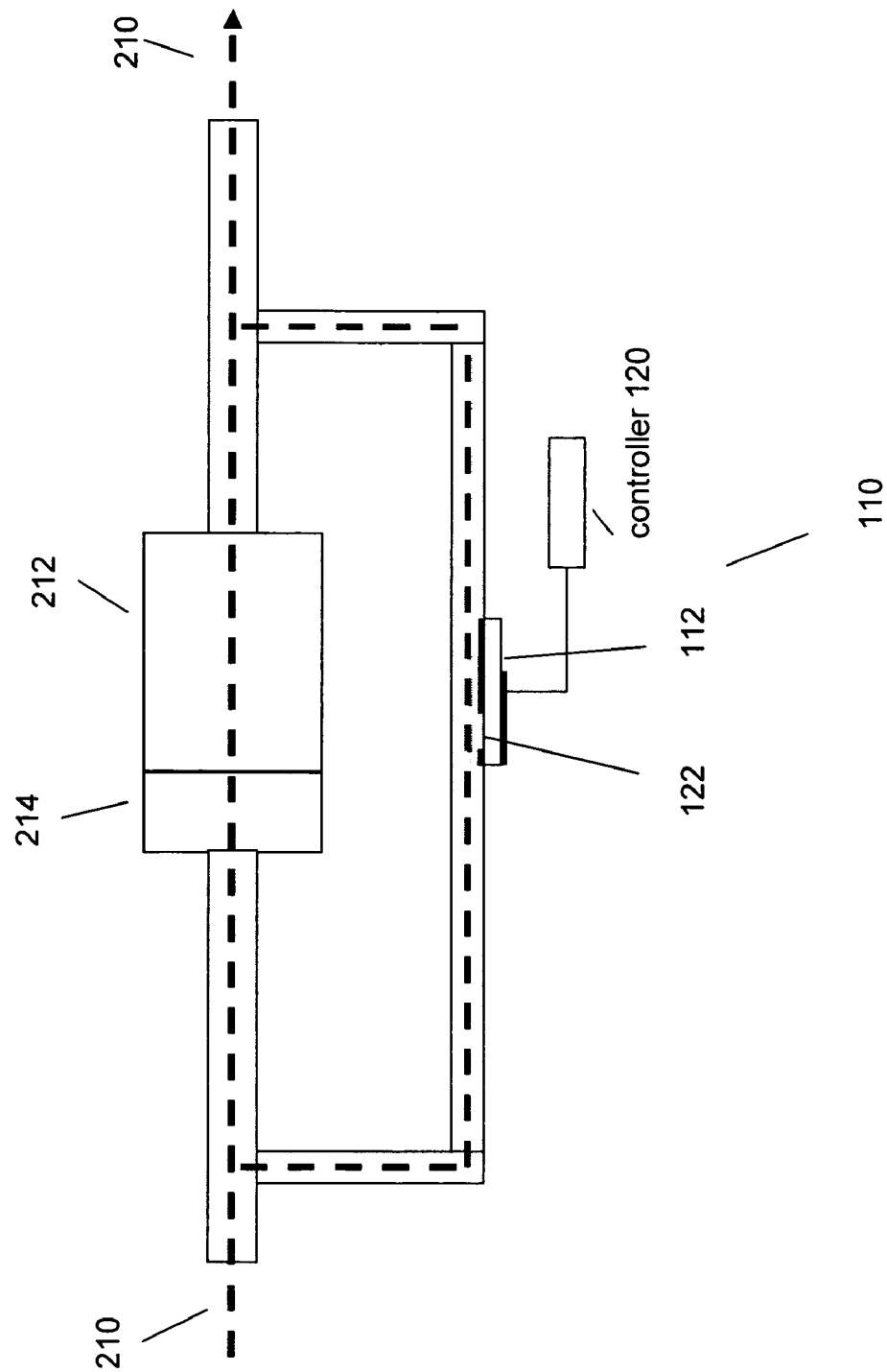
Figure 2C:
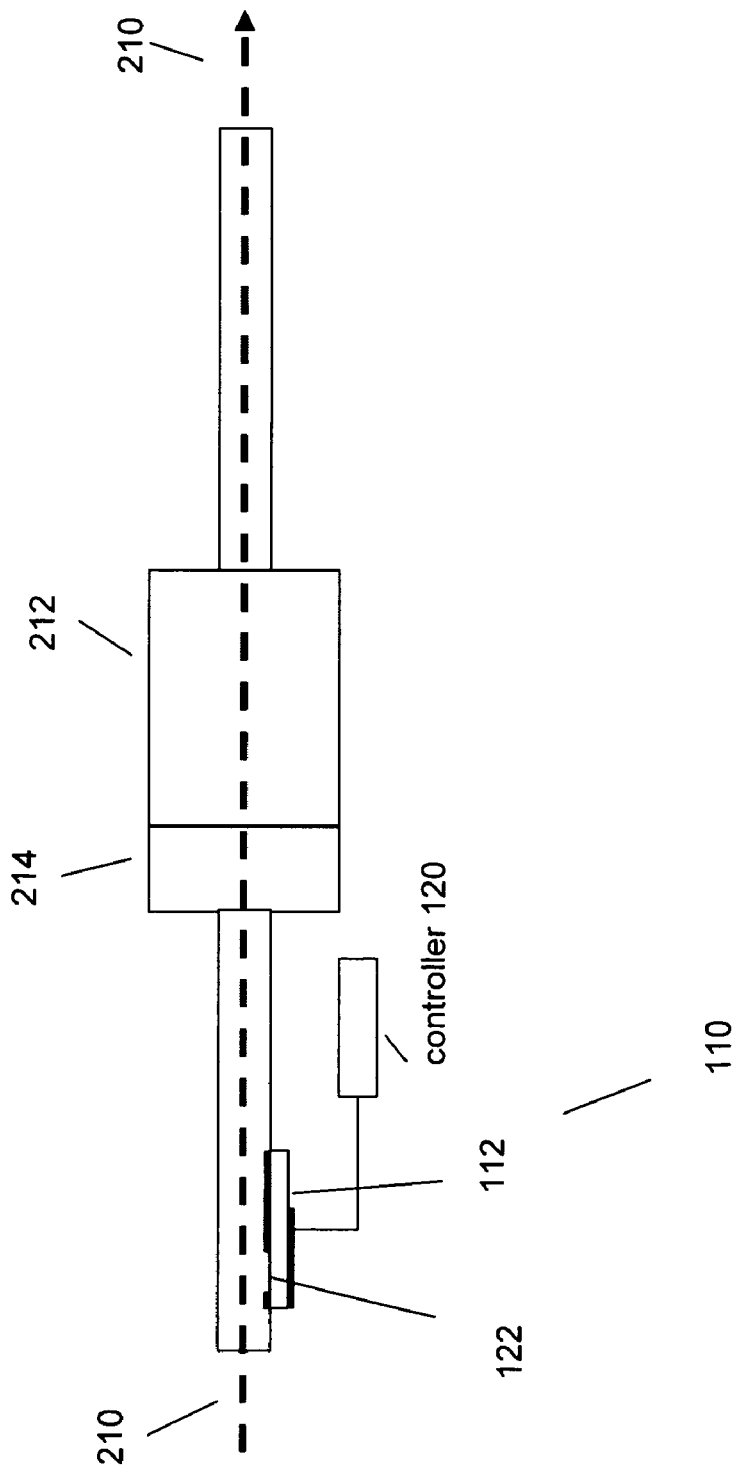

FIGS. 2A, 2B, and 2C shows sensor 110 brought into contact with a fluid flow 210. The fluid flow is combined with the sensor typically at a temperature of at least about 500° C., more typically at a temperature of at least about 600° C. In some embodiments of the invention, the fluid flow is an exhaust stream from a combustion process, e.g., external combustors such as furnaces, boilers, burners, and the like, or in other embodiments of the invention, exhaust streams from internal combustion engines, e.g., four stroke engines, two stroke engines, diesel engines, and the like. In still other embodiments of the invention the fluid flow is an exhaust stream of turbine engines, e.g., jet engines, gas turbines, and the like. In some embodiments of the invention, the gas component of a chemical reaction process, typically gaseous, is measured, for example, the fluid flow can be a gas stream in pyrolysis or cracking of chemicals from various chemical feedstocks, for example, in hydrocarbon "cracking" in petroleum refining, and the like. Typically, the fluid flow is an exhaust stream of an internal combustion engine, e.g., a gasoline four stroke engine or a Diesel engine.

FIG. 2A shows the sensor operating in conjunction with gas trap 212 (see, for example, the Lean $NO_x$ Trap (LNT) described in Y W; Kim, J; Sun, I; Kolmanovsky, J; Koncsol, *SAE Technical Paper Series*, 2003-01-1164 (2003), the entire teachings of which are incorporated herein by reference). The fluid flow 210 is combined with gas trap 212, which includes a second gas-absorbing layer, thereby removing at least a portion of the gas from the fluid flow. The LNT trap typically includes or operates in conjunction with platinum catalyst 214 which can convert at least a portion of NO in $NO_x$ to $NO_2$. As shown in FIG. 2A, sensor 110 is typically located downstream of trap 212 with respect to the flow direction of fluid flow 210 and senses a remaining amount of gas in fluid flow 210 after combining the fluid flow with gas trap 212. Thus, when the gas absorbing layer in trap 212 becomes saturated with gas, the concentration of the gas contacting sensor 110 rises, and controller 120 can correlate this rising gas signal at sensor 110 with a saturated gas condition at trap 212. In other embodiments of the invention, by employing knowledge of the operating characteristics of the engine in conjunction with the absorption characteristics of the trap, a model of the trap condition as a function of sensor condition can be created, so that sensor 110 can be located at other positions on stream 210 with respect to trap 212. For example, in various embodiments of the invention, sensor 110 can be located in parallel with trap 212 with respect to the direction of fluid flow 210 (FIG. 2B), or sensor 110 can be located in series upstream of trap 212 with respect to the direction of fluid flow 210 (FIG. 2C).

Figure 3:
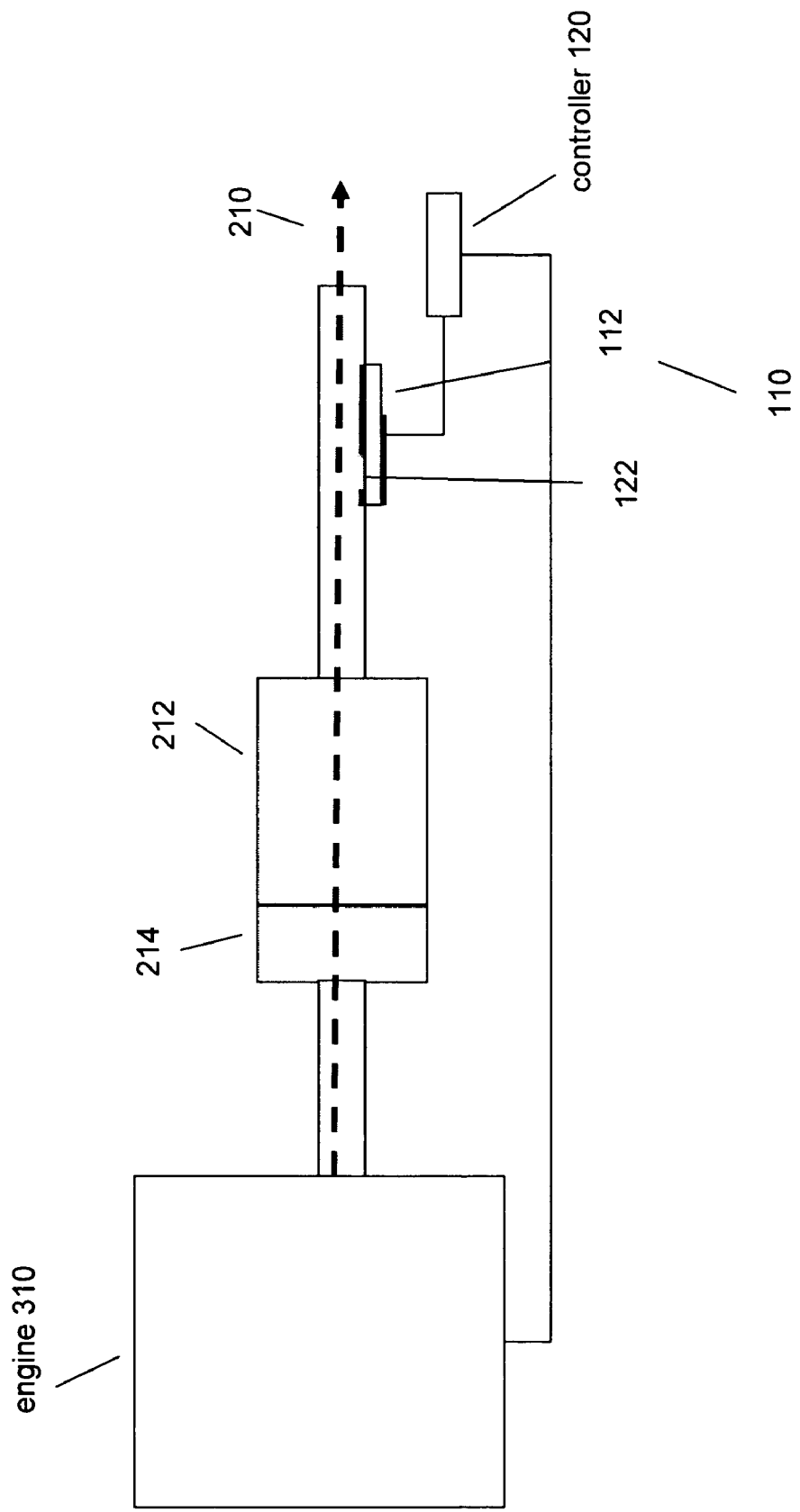
FIG. 3 depicts the system of FIG. 2A in conjunction with an internal combustion engine 310, e.g., wherein the fluid flow 210 is the exhaust stream from engine 310.

In FIG. 3, in further embodiments of the invention, for example, when the first gas absorbing layer 122 is barium carbonate, the gas sensed is $NO_x$, and the fluid flow is an exhaust stream 210 from an internal combustion engine 310, the method includes correlating the remaining amount of $NO_x$ with a saturated $NO_x$ trap condition or an unsaturated $NO_x$ trap condition at trap 212. Also included within the scope of one embodiment of the invention is operating engine 310 (e.g., at the direction of controller 120) in a lean burn mode upon detecting an unsaturated $NO_x$ trap condition, thereby absorbing at least a portion of $NO_x$ resulting from the lean burn condition into trap 212; and operating the engine in a rich burn mode upon detecting a saturated $NO_x$ trap condition, thereby purging trap 212 of at least a portion of $NO_x$ absorbed in the trap and reducing at least a portion of the purged $NO_x$ to $N_2$.

Figure 4:
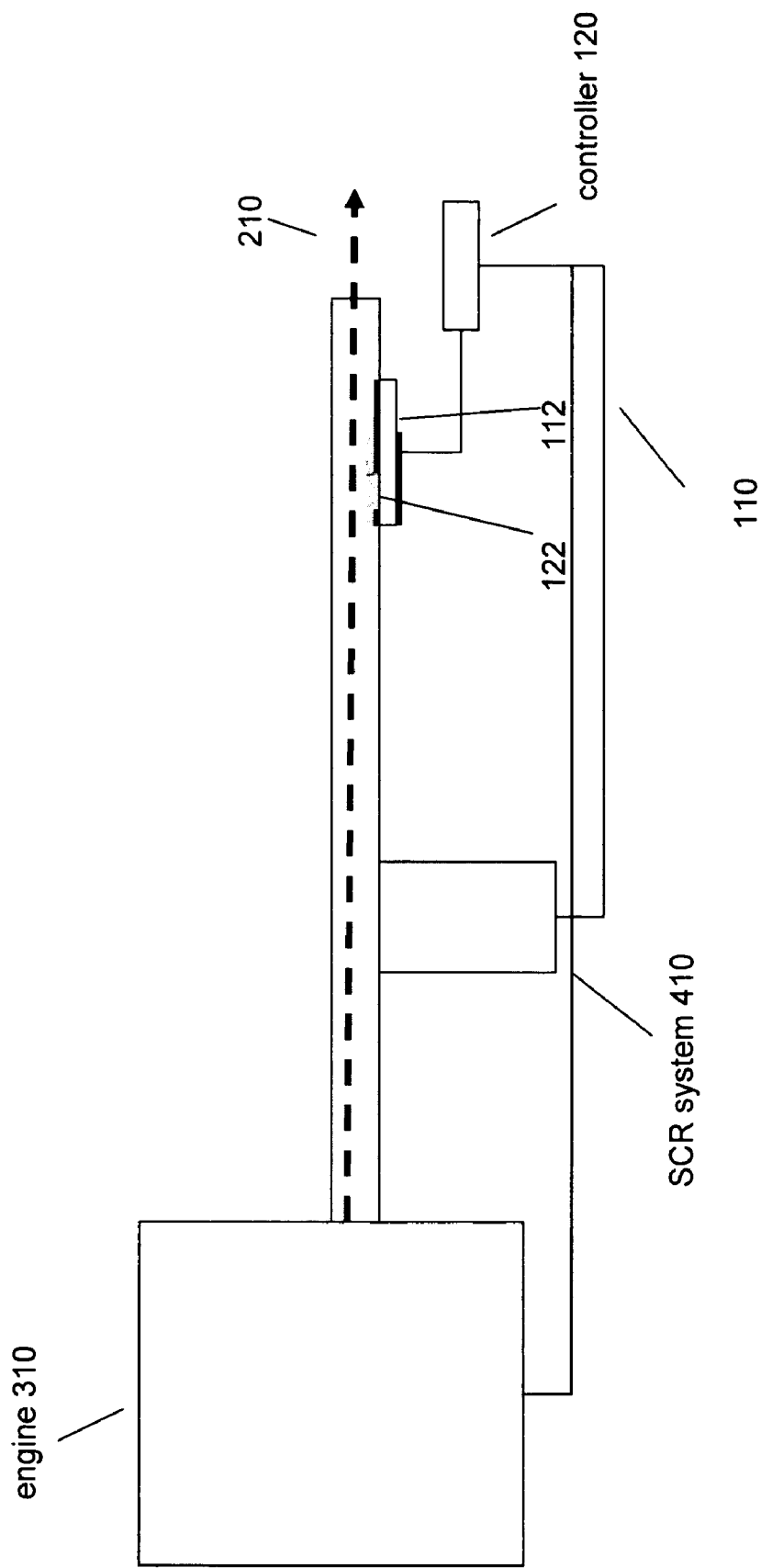
FIG. 4 depicts embodiments of the invention wherein sensor 110 is coupled with a selective catalytic reduction system 410.

FIG. 4 depicts embodiments of the invention wherein the gas sensed is ammonia, e.g., gas absorbing layer 122 is typically a zeolite having pore sizes between about 0.5 nm and about 0.6 nm. For example, in some combustion systems that produce $NO_x$, a selective catalytic reduction (SCR) system 410 with an ammonia feed (e.g., a source of gaseous or liquid ammonia, or a precursor, e.g., urea, which can form ammonia in the engine) injector can be employed. Typically, SCR 410 introduces urea as the feed, which decomposes to form ammonia, which can then react with the $NO_x$ to reduce it to $N_2$. For example, some embodiments of the invention include sensing between about 2 parts per million (ppm) and about 100 ppm of ammonia in the fluid flow; comparing the amount of ammonia to an amount of ammonia that will selectively catalytically reduce at least a portion of $NO_x$ to $N_2$ in fluid flow 210; and injecting an amount of ammonia feed, e.g., urea, corresponding to the amount of ammonia that will selectively catalytically reduce at least a portion of $NO_x$ to $N_2$ in fluid flow 210. Controller 120 is coupled, e.g., is in electronic communication with SCR 410, whereby the appropriate amount of ammonia feed, e.g., urea, can be injected.

Figure 5:
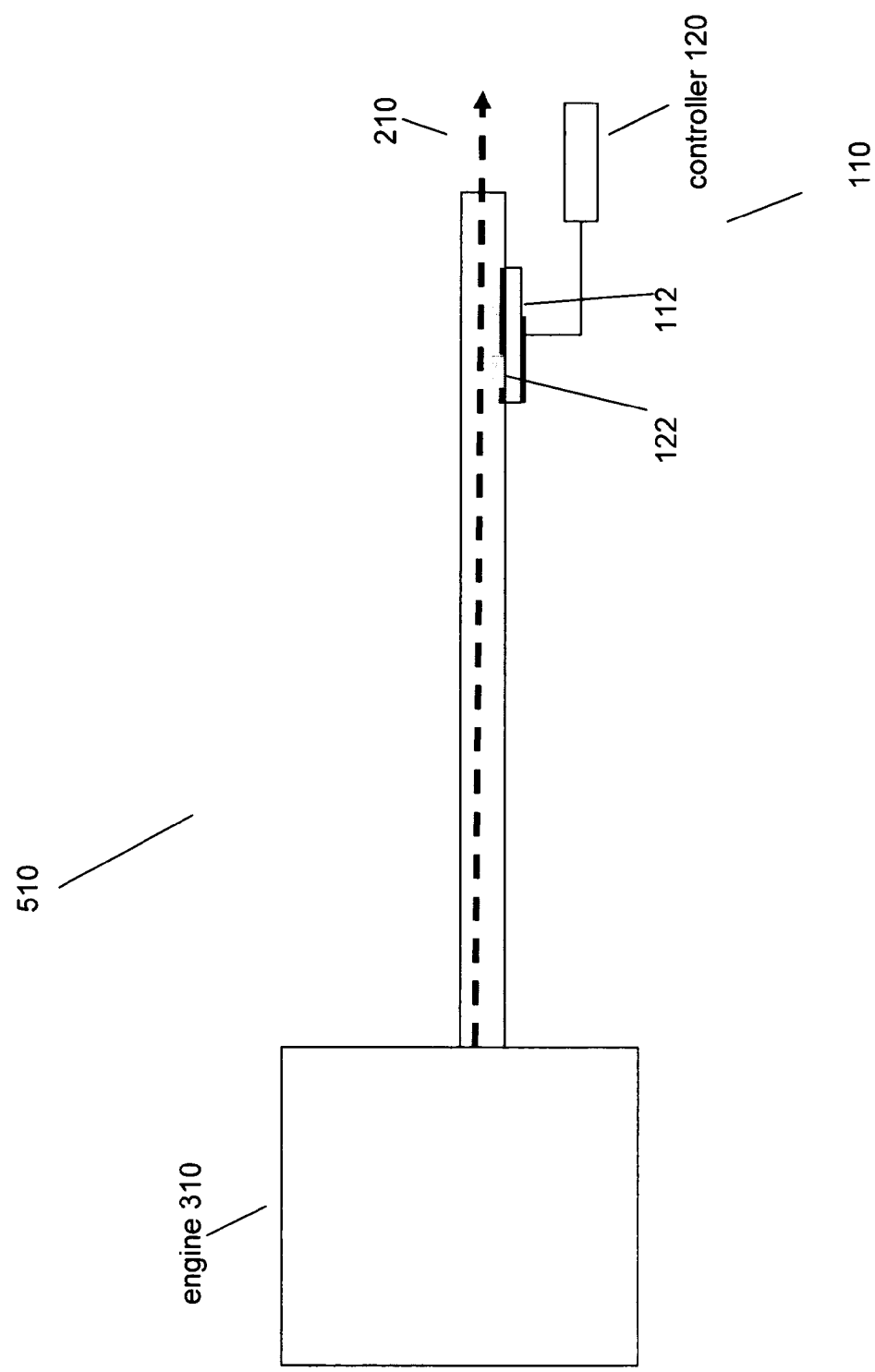
FIG. 5 depicts an embodiment of a system 510 for sensing $NO_x$ in conjunction with LNT 212 coupled with an internal combustion engine 310 in an embodiment of the method of the invention.

FIG. 5 depicts an embodiment of AW sensor 110 of the invention for sensing the amount of a $NO_x$ component in an exhaust stream 210 of an internal combustion engine 310, which includes a first barium carbonate layer 122 having a surface area to volume ratio of less than about $1 \times 10^7$ $cm^{2:1}$ $cm^3$; a $La_3Ga_5SiO_{14}$ high temperature stable piezoelectric plate 112 coupled to first barium carbonate layer 122; and controller 120 coupled to $La_3Ga_5SiO_{14}$ high temperature stable piezoelectric plate 112 that correlates a resonant frequency in high temperature stable piezoelectric plate 112 with an amount of $NO_x$ absorbed by first barium carbonate layer 122, whereby the amount of $NO_x$ in exhaust stream 210 of internal combustion engine 310 is sensed. In other embodiments of the invention, a method of sensing the amount of $NO_x$ in an exhaust stream (e.g., stream 210) from an internal combustion engine (e.g., engine 310) includes operating an acoustic wave (AW) sensor (e.g., AW sensor 110) at a resonant frequency, the AW sensor having a $La_3Ga_5SiO_{14}$ high temperature stable piezoelectric plate (e.g., plate 112) coupled to a barium carbonate layer (e.g., layer 122); combining an exhaust stream including a $NO_x$ component with the barium carbonate layer at a temperature of at least about 500° C., thereby reacting at least a portion of the $NO_x$ component with the barium carbonate layer to form barium nitrate; sensing at least one resonant frequency of the high temperature stable piezoelectric plate; and correlating the resonant frequency with the amount of $NO_x$ reacted to form barium nitrate, thereby sensing the amount of $NO_x$ in the exhaust stream.

Figure 6:
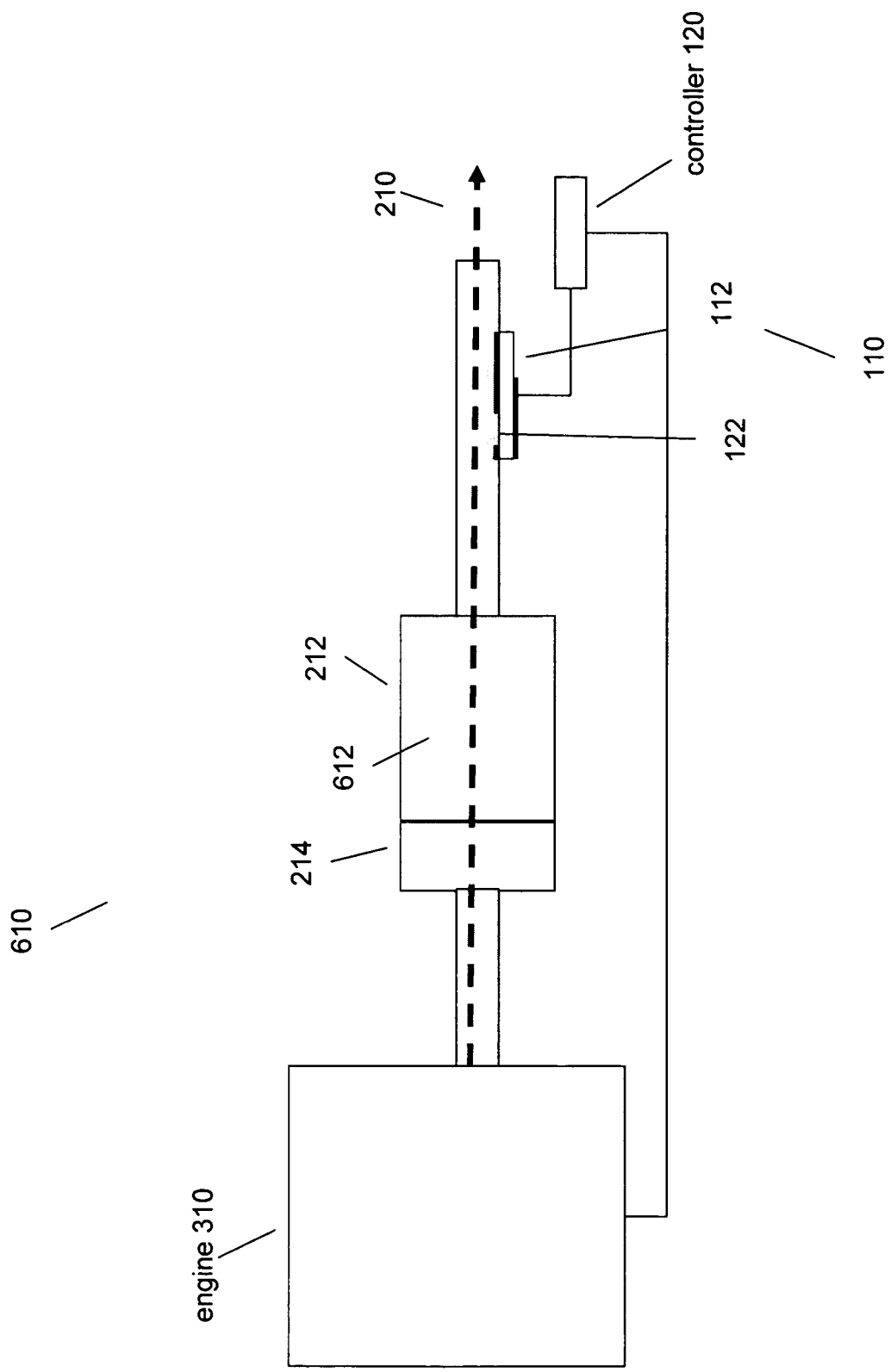
FIG. 6 depicts an embodiment of a system 610 for reducing $NO_x$ to $N_2$ in exhaust stream 210 of internal combustion engine 310 in conjunction with LNT 212 in an embodiment of the method of the invention.

FIG. 6 depicts a system 610 for reducing $NO_x$ to $N_2$ in exhaust stream 210 of internal combustion engine 310. System 610 includes $NO_x$ sensor 110 including first barium carbonate layer 122 having a surface area to volume ratio of less than about $1 \times 10^7$ $cm^7:1$ $cm^3$, and $La_3Ga_5SiO_{14}$ high temperature stable piezoelectric plate 112 coupled to first barium carbonate layer 122; $NO_x$ trap 212 coupled in series with $NO_x$ sensor 110, $NO_x$ trap 212 including a second barium carbonate layer 612, the $NO_x$ sensor being located downstream of the $NO_x$ trap with respect to the flow direction of exhaust stream 210 from internal combustion engine 310; and controller 120. Controller 120 is coupled to $La_3Ga_5SiO_{14}$ high temperature stable piezoelectric plate 112 to sense a resonant frequency in the high temperature stable piezoelectric plate, and is in electronic communication with internal combustion engine 310 to direct the engine to operate in a lean burn mode and a rich burn mode, whereby at least a portion of $NO_x$ is reduced to $N_2$ in exhaust stream 210 of internal combustion engine 310. In other embodiments of the invention, a method of reducing $NO_x$ to $N_2$ in the exhaust stream (e.g., stream 210) of an internal combustion engine (e.g., engine 310) includes directing an exhaust stream including a $NO_x$ component from an internal combustion engine to a $NO_x$ trap (e.g., trap 212) coupled in series with an acoustic wave (AW) $NO_x$ sensor (e.g., sensor 110), thereby reacting at least a portion of the $NO_x$ component with barium carbonate to form barium nitrate. The trap includes a second barium carbonate layer (e.g., layer 612); and the AW sensor, located downstream of the trap with respect to the flow of the exhaust stream, includes a $La_3Ga_5SiO_{14}$ high temperature stable piezoelectric plate (e.g., plate 112) coupled to the first barium carbonate layer. Also included within the scope of this invention is sensing at least one resonant frequency of the high temperature stable piezoelectric plate; correlating the resonant frequency with the amount of $NO_x$ absorbed in the first barium carbonate layer, thereby sensing a saturated $NO_x$ trap condition and an unsaturated $NO_x$ trap condition; operating the engine in a lean burn mode upon sensing an unsaturated $NO_x$ trap condition, thereby reacting at least a portion of $NO_x$ resulting from the lean burn condition with the second barium carbonate layer to form barium nitrate; and operating the engine in a rich burn mode upon sensing a saturated $NO_x$ trap condition, thereby purging at least a portion of the barium carbonate layers (e.g., layers 122 and 612) of barium nitrate to release $NO_x$, and reducing at least a portion of the released $NO_x$ to $N_2$.

Figure 7:
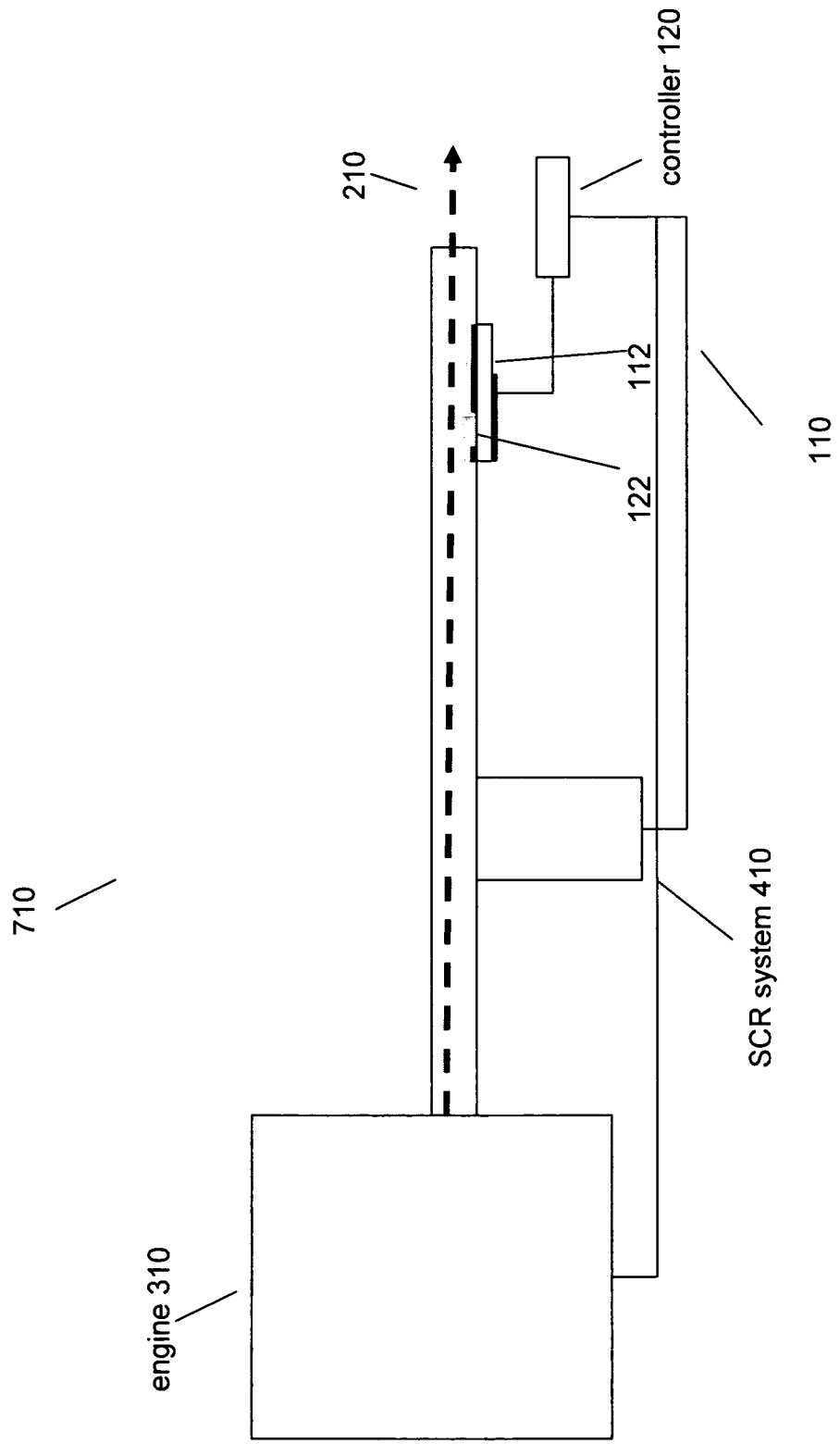
FIG. 7 depicts a sensor 710 for sensing the amount of an ammonia component in exhaust stream 210 of internal combustion engine 310 in an embodiment of the method of the invention.

FIG. 7 depicts a system 710 for sensing the amount of an ammonia component in exhaust stream 210 of internal combustion engine 310. System 710 includes sensor 110, which includes a zeolite gas absorption layer 122 having a surface area to volume ratio of less than about $1 \times 10^7$ $cm^2:1$ $cm^3$, and the zeolite having pore sizes between about 0.5 nm and about 0.6 nm; a $La_3Ga_5SiO_{14}$ high temperature stable piezoelectric plate 112 coupled to zeolite gas absorbing layer 122; and controller 120. Controller 120 is coupled to measure at least one resonant frequency of $La_3Ga_5SiO_{14}$ high temperature stable piezoelectric plate 112 that is correlated with an amount of ammonia absorbed by zeolite gas absorbing layer 122; and controller 120 is coupled to measure at least one electrical complex impedance of the zeolite gas absorbing layer that is correlated with the amount of ammonia absorbed by the zeolite gas absorbing layer, whereby the amount of an ammonia component in an exhaust stream of an internal combustion engine is sensed. In other embodiments of the invention, controller 120 is in electronic communication with a selective catalytic reduction system (SCR) urea injection system 410 coupled to internal combustion engine 310. In some embodiments of the invention, a method of sensing the amount of ammonia in an exhaust stream (e.g., stream 210) from an internal combustion engine (e.g., a diesel engine) includes operating an acoustic wave (AW) sensor (e.g., sensor 110) at a resonant frequency, the AW sensor having a $La_3Ga_5SiO_{14}$ high temperature stable piezoelectric plate (e.g., plate 112) coupled to a zeolite gas absorbing layer (e.g., layer 122), the zeolite having a pore size between about 0.5 nm and about 0.6 nm; combining an exhaust stream including an ammonia component with the zeolite gas absorbing layer at a temperature of at least about 500° C., thereby absorbing at least a portion of the ammonia into the zeolite gas absorbing layer; sensing at least one resonant frequency of the high temperature stable piezoelectric plate, and correlating the resonant frequency with the amount of ammonia absorbed in the zeolite gas absorbing layer; sensing the electrical complex impedance of the zeolite gas absorbing layer, and correlating the electrical complex impedance with the amount of ammonia absorbed in the zeolite gas absorbing layer, and comparing the amount of ammonia absorbed in the zeolite gas absorbing layer according to the frequency and the electrical complex impedance, thereby sensing the amount of ammonia in the exhaust stream. Other embodiments of the invention include comparing the amount of ammonia in the exhaust stream to an amount of ammonia that will selectively catalytically reduce at least a portion of $NO_x$ in the exhaust stream to $N_2$; and injecting (e.g., with SCR system 714) an amount of urea corresponding to the amount of ammonia that will selectively catalytically reduce at least a portion of $NO_x$ to $N_2$ in the exhaust stream.

In some embodiments of the invention, a piezoelectric plate made of any piezoelectric material is coupled to a metal carbonate gas absorbing layer, for example, any of the high temperature stable piezoelectric materials above, and also "conventional piezoelectric materials", e.g., quartz, $LiNbO_3$, $Li_2B_4O_7$, ZnO, lead zirconate titanate (PZT), and $LiTaO_3$. Thus, as used herein, in some embodiments of the invention, "piezoelectric materials" used in a piezoelectric plate that is not specified as "high temperature stable" include both "high temperature stable piezoelectric materials" and "conventional piezoelectric materials, for example, "piezoelectric materials" include AlN, GaN, $Al_{1-x}Ga_xN$ ($0 \leq x \leq 1$), $GaPO_4$, $AlPO_4$, and materials having the crystal structure of $Ca_2Ga_2Ge_4SiO_{14}$, e.g., $Ca_2Ga_2Ge_4SiO_{14}$, $La_3Ga_5SiO_{14}$, $La_3Ga_{5.5}Nb_{0.5}O_{14}$, $La_3Ga_{5.5}Ta_{0.5}O_{14}$, and the like; and quartz, $LiNbO_3$, $Li_2B_4O_7$, ZNO, lead zirconate titanate (PZT), and $LiTaO_3$.

Thus, in various embodiments of the invention, a method of sensing the amount of a gas component in a fluid flow includes the steps of operating an acoustic wave (AW) sensor at a first resonant frequency, the AW sensor including a piezoelectric plate coupled to a first gas-absorbing layer, the gas absorbing layer comprising a metal carbonate; combining a fluid flow having a gas component with the first gas-absorbing layer; and sensing at least one resonant frequency of the AW sensor, whereby the resonant frequency can be correlated with the amount of gas absorbed in the first gas-absorbing layer, thereby sensing the amount of gas in the fluid flow. In some embodiments, the piezoelectric plate is formed of one or more materials selected from the group consisting of AlN, GaN, $Al_{1-x}Ga_xN$ ($0 \leq x \leq 1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$. Typically, the first gas-absorbing layer has a surface area to volume ratio of less than about $1 \times 10^7$ $cm^2$:1$cm^3$; or the first gas-absorbing layer has a gas absorption/adsorption ratio of at least about 2000:1; or, the first gas-absorbing layer has an ordered microstructure of micropores between about 200 nm and about 3000 nm in diameter. The fluid flow is selected from the group consisting of an exhaust stream from an external combustion process, a gas stream in a pyrolysis process, and an exhaust stream from an internal combustion engine. Typically, the fluid flow is an exhaust stream from an internal combustion engine. Generally, the first gas-absorbing layer includes barium carbonate.

In various embodiments of the invention, an acoustic wave (AW) sensor for sensing the amount of a gas in a fluid flow includes a first gas-absorbing layer comprising a metal carbonate; a piezoelectric plate coupled to the first gas-absorbing layer; and a controller coupled to the piezoelectric plate to measure a resonant frequency piezoelectric plate correlated with an amount of gas absorbed by the first gas absorbing layer, whereby the amount of a gas in a fluid flow is sensed. In some embodiments, the piezoelectric plate is formed of one or more materials selected from the group consisting of AlN, GaN, $Al_{1-x}Ga_xN$ ($0 \leq x \leq 1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$. Generally, the first gas-absorbing layer has a surface area to volume ratio of less than about $1 \times 10^7$ $cm^2$:1 $cm^3$; or the first gas-absorbing layer has a gas absorption/adsorption ratio of at least about 2000:1; or the first gas-absorbing layer has an ordered microstructure of micropores between about 200 nm and about 3000 nm in diameter. The AW sensor can be coupled with a fluid flow selected from the group consisting of an exhaust stream from an external combustion process, a gas stream in a pyrolysis process, and an exhaust stream from an internal combustion engine, typically an exhaust stream from an internal combustion engine. In various embodiments of the invention, the first gas-absorbing layer includes barium carbonate.

In some embodiments of the invention, a method of sensing the amount of a gas component in a fluid flow, includes the steps of operating an acoustic wave (AW) sensor at a first resonant frequency, the AW sensor including a piezoelectric plate coupled to a first gas-absorbing layer, the gas absorbing layer including a metal carbonate or a zeolite; combining a fluid flow having a gas component with the first gas-absorbing layer; sensing at least one resonant frequency of the AW sensor; and sensing at least one electrical complex impedance value of the gas-absorbing layer, whereby the resonant frequency can be correlated with the amount of gas absorbed in the first gas-absorbing layer, and the electrical complex impedance value of the gas-absorbing layer can be correlated with the amount of gas absorbed by the first gas absorbing layer, thereby sensing the amount of gas in the fluid flow.

In some embodiments of the invention, an acoustic wave (AW) sensor for sensing the amount of a gas in a fluid flow includes: a first gas-absorbing layer including a metal carbonate or a zeolite; a piezoelectric plate coupled to the first gas-absorbing layer; and a controller. The controller is coupled to the piezoelectric plate to measure a resonant frequency piezoelectric plate correlated with an amount of gas absorbed by the first gas absorbing layer; and is coupled to the gas absorbing layer to measure an electrical complex impedance value correlated with an amount of gas absorbed by the first gas absorbing layer, whereby the amount of a gas in a fluid flow is sensed.

EXEMPLIFICATION

The invention is further illustrated by the following example. It is to be understood, however, that although this example may specifically describe particular aspects of this invention, it is primarily for purposes of illustration, and the invention in its broader aspects is not to be construed as limited thereto.

Example 1

Quartz/Barium Carbonate Sensor Detects $NO_x$

Figures 8A, 8B:
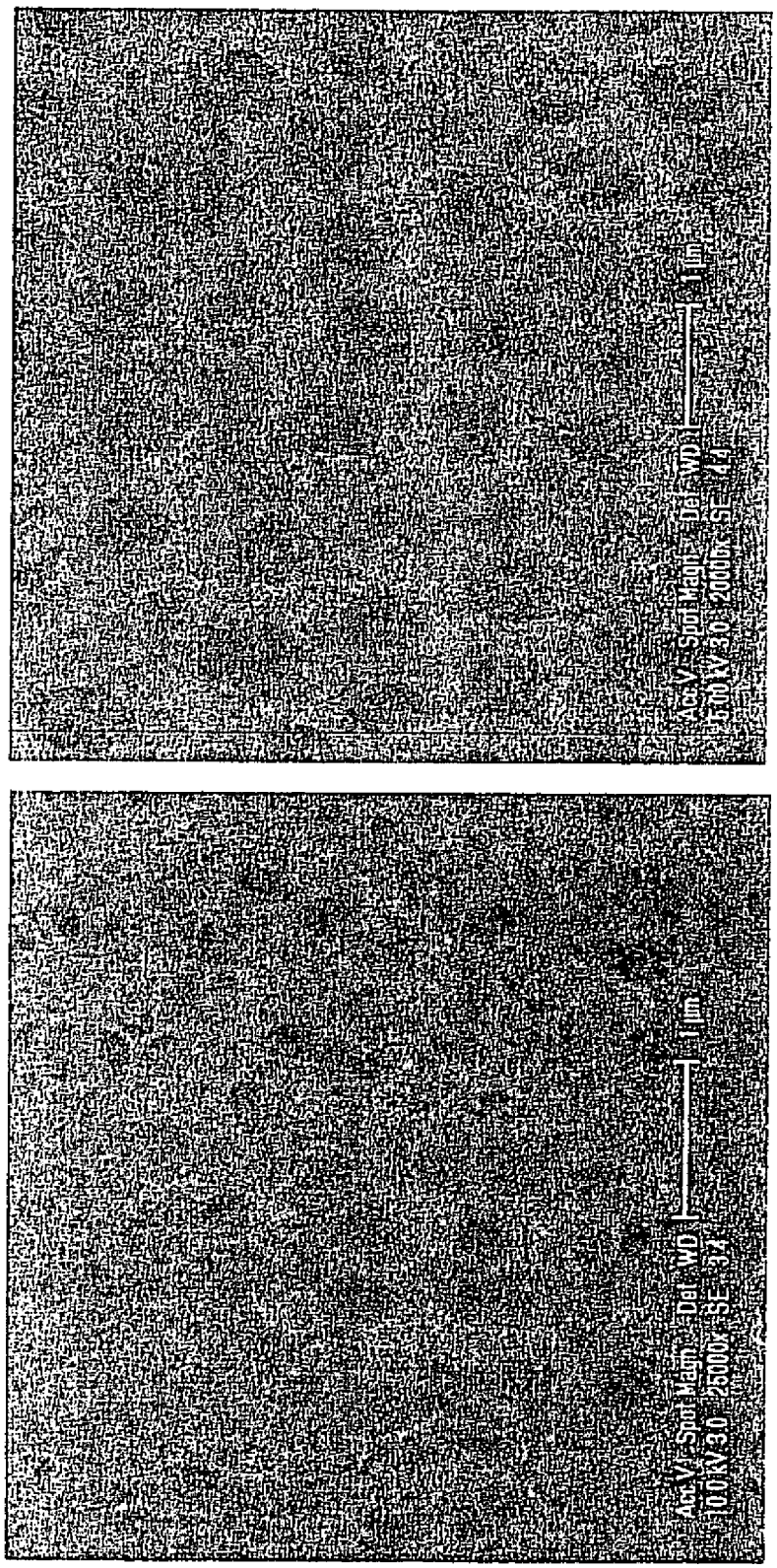
FIGS. 8A and 8B show scanning electron microscope pictures of microporous barium carbonate layers templated with 400 nm (8A) or 800 nm (8B) poly methyl methacrylate (PMMA) microspheres.

A layer of barium carbonate was deposited on the surface of a quartz AW sensor by adapting the methods described in Sasahara, K; Hyodo, T; Shimizu, Y; Egashira, M; J. European Ceramic Soc., 24, 1961–1967, (2001), the entire teachings of which are incorporated herein by reference. Briefly, a barium carbonate film was deposited using a PMMA templating technique. About 0.2 g of PMMA microspheres (800 nm or 400 nm in diameter, Soken Chem. & Eng. Co., Ltd.) was dispersed in 10 ml deionized water, and the suspension was dripped by pipette onto a piezoelectric sensor and allowed to dry at room temperature. A precursor solution of 2M aqueous barium acetate was allowed to permeate the PMMA microspheres, in vacuo, at room temperature. Thereafter, the resultant film was subjected to heat treatment at 400° C. for 2 h to remove the PMMA microspheres through thermal decomposition, resulting in a microporous barium carbonate framework. Scanning electron microscopy revealed the resulting barium carbonate layer to have a regular microstructure of micropores of approximately the size of the PMMA template microspheres (FIG. 8A, 400 nm; FIG. 8B, 800 nm), and a layer thickness of about 2 µm thick. X-ray diffraction confirmed the layer to be single phase barium carbonate. These layers were observed to exhibit well-defined microstructures and high microporosity which can be desirable in gas sensor applications.

The resonant sensor, together with a blank reference sensor, was installed in a sensor holder and then inserted into a furnace. Temperatures from about 250° C. to about 400° C. at about 50° C. increments were selected for study and were recorded with a thermocouple sited close to the sensor. Gas compositions were controlled using mass flow controllers by varying the flow rate of 100 ppm $NO_2$/Ar, pure Ar and $CO/CO_2$ gas mixtures. The resonant frequency was obtained by using the built-in fitting routine (4-elements equivalent circuit model) of a network analyzer (Agilent E5100A, Agilent, Palo Alto, Calif.). Readings were taken approximately every 15 seconds using Labview (National Instruments, Dallas, Tex.) software. During testing, the sensor was equilibrated in Ar for 15 min, exposed to 100 ppm $NO_2$/Ar for 30 min, reduced in 50% $CO/CO_2$ mixtures for another 30 min, and finally flushed with Ar for 15 min.

Figure 9:
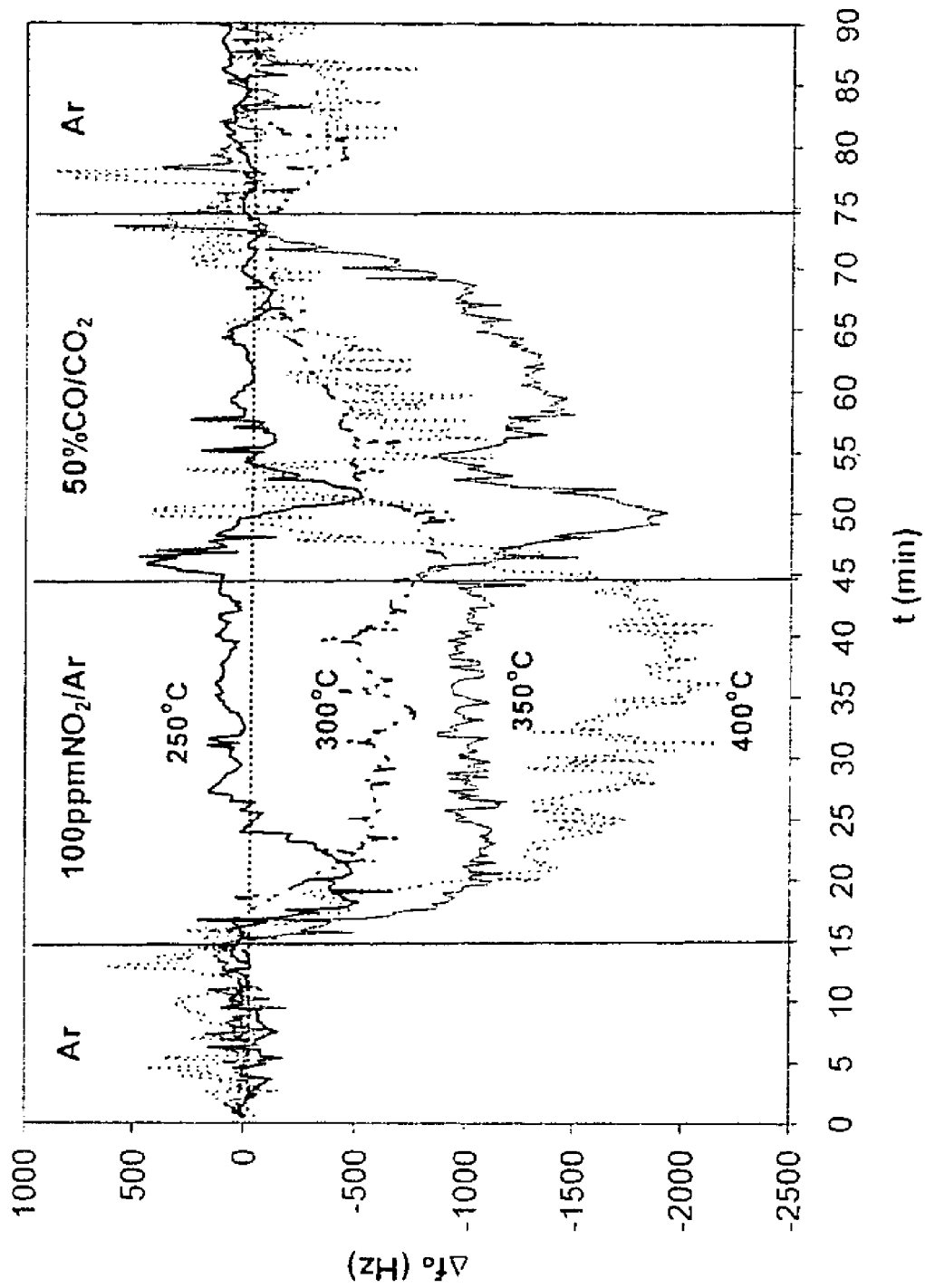
FIG. 9 is a graph of the response of a piezoelectric sensor coated with barium carbonate (templated with 400 nm PMMA microspheres) to $NO_2$ at various temperatures.

The changes in $f_o$ (defined as the different frequency between the sensor and the reference ($f_o = f_s - f_{ref}$)) of a sensor coated with a $BaCO_3$ film (fabricated from the 400 nm PMMA template) after exposure to 100 ppm $NO_2$ and subsequent recovery are shown in FIG. 9.

Sensitivity to $NO_2$ is observed for temperatures of 300° C. and above, with full recovery upon introduction of $CO/CO_2$. The large fluctuations around 15, 45 and 75 min resulted from gas switching.

A sensor employing langasite or other high temperature stable piezoelectric plate materials provided herein can be constructed by methods described in Tuller, H L and Fritze, H, "Langasite for high temperature bulk acoustic wave applications," *App. Phys. Lett.*, 78, (2001), 976–977; Tuller, et al., "High temperature nanobalance sensor based on langasite,", *Sensors and Actuators*, B 76, (2001), 103–107; Tuller, et al., "Operational limits of langasite high temperature nanobalances,", *J. Euro. Ceramic Soc.*, 21, (2001), 1473–1477. The entire teachings of these references are included herein by reference. Coupling of a high temperature stable piezoelectric plate with a gas absorbing layer, e.g., barium carbonate, can be accomplished by the method above for coupling barium carbonate with a quartz AW sensor.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of sensing the amount of a gas component in a fluid flow, comprising the steps of:
   a) operating an acoustic wave (AW) sensor at a first resonant frequency, the AW sensor including a high temperature stable piezoelectric plate coupled to a first gas-absorbing layer, wherein the first gas-absorbing layer has a surface area to volume ratio of less than about $1 \times 10^7$ $cm^2$: 1 $cm^3$;
   b) combining a fluid flow having a gas component with the first gas-absorbing layer at a temperature of at least about 500° C.; and
   c) sensing at least one resonant frequency of the AW sensor, whereby the resonant frequency can be correlated with the amount of gas absorbed in the first gas-absorbing layer, thereby sensing the amount of gas in the fluid flow.

2. The method of claim 1, wherein the fluid flow is at a temperature of at least about 600° C.

3. The method of claim 1, wherein the high temperature stable piezoelectric plate is formed of one or more materials selected from the group consisting of AlN, GaN, $Al_{1-x}Ga_xN$ ($0 \leq x \leq 1$), $GaPO_4$, $AlPO_4$, and materials having the crystal structure of $Ca_2Ga_2Ge_4SiO_{14}$.

4. The method of claim 3, wherein the high temperature stable piezoelectric plate is formed of one or more materials selected from the group consisting of AlN, $Al_{1-x}Ga_xN$ ($0 < x \leq 1$), $AlPO_4$, $Ca_2Ga_2Ge_4SiO_{14}$, $La_3Ga_5SiO_{14}$, $La_3Ga_{5.5}Nb_{0.5}O_{14}$, and $La_3Ga_{5.5}Ta_{0.5}O_{14}$.

5. The method of claim 4, wherein the high temperature stable piezoelectric plate consists essentially of $La_3Ga_5SiO_{14}$.

6. A method of sensing the amount of a gas component in a fluid flow, comprising the steps of:
   a) operating an acoustic wave (AW) sensor at a first resonant frequency, the AW sensor including a high temperature stable piezoelectric plate coupled to a first gas-absorbing layer, wherein the first gas-absorbing layer has a surface area to volume ratio of less than about $1 \times 10^7$ $cm^2$: 1 $cm^3$;
   b) combining a fluid flow having a gas component with the first gas-absorbing layer at a temperature of at least about 500° C.; and
   c) sensing at least one resonant frequency of the AW sensor, whereby the resonant frequency can be correlated with the amount of gas absorbed in the first gas-absorbing layer, thereby sensing the amount of gas in the fluid flow, wherein the high temperature stable piezoelectric plate is formed of one or more materials selected from the group consisting of AlN, $Al_{1-x}Ga_xN$ ($0 < x \leq 1$), $AlPO_4$, $Ca_2Ga_2Ge_4SiO_{14}$, $La_3Ga_5SiO_{14}$, $La_3Ga_{5.5}Nb_{0.5}O_{14}$, and wherein the first gas-absorbing layer includes one or more materials selected from the group consisting of metal carbonates and zeolites.

7. The method of claim 6, wherein the fluid flow is an exhaust stream from an external combustion process.

8. The method of claim 6, wherein the fluid flow is a gas stream in a pyrolysis process.

9. The method of claim 6, wherein the fluid flow is an exhaust stream from an internal combustion engine.

10. The method of claim 9, further including sensing the gas in conjunction with a gas trap, including:
    a) combining the fluid flow with a gas trap, the trap including a second gas-absorbing layer, thereby removing at least a portion of the gas from the fluid flow; and
    b) sensing a remaining amount of gas in the fluid flow after combining the fluid flow with the gas trap.

11. The method of claim 10, wherein the first gas-absorbing layer includes barium carbonate.

12. The method of claim 11, wherein the gas sensed in the fluid flow is $NO_x$.

13. The method of claim 12, further including:
    a) correlating the remaining amount of $NO_x$ with a saturated $NO_x$ trap condition or an unsaturated $NO_x$ trap condition;
    b) operating the engine in a lean burn mode upon detecting an unsaturated $NO_x$ trap condition, thereby absorbing at least a portion of $NO_x$ resulting from the lean burn condition into the $NO_x$ trap; and c) operating the engine in a rich burn mode upon detecting a saturated $NO_x$ trap condition, thereby purging the trap of at least a portion of $NO_x$ absorbed in the trap and reducing at least a portion of the purged $NO_x$ to $N_2$.

14. The method of claim 9, wherein the first gas-absorbing layer includes a zeolite selected from Linde Type A, zeolite beta, NaX, NaA, NaY, ZSM-5, H-ZSM-5, natrolite, chabazite, sodalite, faujasite, mordenite, MCM-41, MCM-48, and MCM-50.

15. The method of claim 14, wherein at least two electrodes are applied to the AW sensor, further including sensing and correlating at least one electrical complex impedance for the first gas-absorbing layer with the amount of gas absorbed, thereby sensing the amount of gas in the fluid flow.

16. The method of claim 15, further including comparing the amount of gas sensed from both the frequency of the high temperature stable piezoelectric plate and the electrical complex impedance of the first gas absorbing layer.

17. The method of claim 16, wherein the gas sensed is ammonia.

18. The method of claim 17, further including:
a) sensing between about 2 parts per million (ppm) and about 100 ppm of ammonia in the fluid flow;
b) comparing the amount of ammonia to an amount of ammonia that will selectively catalytically reduce at least a portion of $NO_x$ to $N_2$ in the fluid flow; and
c) injecting an amount of urea corresponding to the amount of ammonia that will selectively catalytically reduce at least a portion of $NO_x$ to $N_2$ in the fluid flow.

19. A method of sensing the amount of a gas component in a fluid flow, comprising the steps of:
a) operating an acoustic wave (AW) sensor at a first resonant frequency, the AW sensor including a high temperature stable piezoelectric elate coupled to a first gas-absorbing layer, wherein the first gas-absorbing layer has a gas absorption/adsorption ratio of at least about 2000:1;
b) combining a fluid flow having a gas component with the first gas-absorbing layer at a temperature of at least about 500° C.: and
c) sensing at least one resonant frequency of the AW sensor, whereby the resonant frequency can be correlated with the amount of gas absorbed in the first gas-absorbing layer, thereby sensing the amount of gas in the fluid flow,
wherein the high temperature stable piezoelectric plate is formed of one or more materials selected from the group consisting of AlN, $Al_{1-x}Ga_xN$ (0<x≦1), $AlPO_4$, $Ca_2Ga_2Ge_4SiO_{14}$, $La_3Ga_5SiO_{14}$, $La_3Ga_{5.5}Nb_{0.5}O_{14}$, and $La_3Ga_{5.5}Ta_{0.5}O_{14}$, and wherein the first gas-absorbing layer includes one or more materials selected from the group consisting of metal carbonates and zeolites.

20. A method of sensing the amount of a gas component in a fluid flow, comprising the steps of:
a) operating an acoustic wave (AW) sensor at a first resonant frequency, the AW sensor including a high temperature stable piezoelectric plate coupled to a first gas-absorbing layer, wherein the first gas-absorbing layer has an ordered microstructure of micropores between about 200 nm and about 3000 nm in diameter;
b) combining a fluid flow having a gas component with the first gas-absorbing layer at a temperature of at least about 500° C.; and
c) sensing at least one resonant frequency of the AW sensor, whereby the resonant frequency can be correlated with the amount of gas absorbed in the first gas-absorbing layer, thereby sensing the amount of gas in the fluid flow,
wherein the high temperature stable piezoelectric plate is formed of one or more materials selected from the group consisting of AlN, $Al_{1-x}Ga_xN$ (0<x≦1), $AlPO_4$, $Ca_2Ga_2Ge_4SiO_{14}$, $La_3Ga_5SiO_{14}$, $La_3Ga_{5.5}Nb_{0.5}O_{14}$, and $La_3Ga_{5.5}Ta_{0.5}O_{14}$, and wherein the first gas-absorbing layer includes one or more materials selected from the group consisting of metal carbonates and zeolites.

21. An acoustic wave (AW) sensor for sensing the amount of a gas in a fluid flow, comprising:
a) a first gas-absorbing layer;
b) a high-temperature-stable piezoelectric plate coupled to the first gas-absorbing layer, the high-temperature-stable piezoelectric plate including at least one material selected from the group consisting of AlN, GaN, $Al_{1-x}Ga_xN$ (0≦x≦1), $GaPO_4$, $AlPO_4$, and materials having the crystal structure of $Ca_2Ga_2Ge_4SiO_{14}$, the first gas-absorbing layer having a surface area to volume ratio of less than about $1 \times 10^7$ $cm^2$: 1 $cm^3$; and
c) a controller coupled to the high-temperature-stable piezoelectric plate to measure a resonant frequency in the high temperature stable piezoelectric plate correlated with an amount of gas absorbed by the first gas absorbing layer,
whereby the amount of a gas in a fluid flow is sensed.

22. An acoustic wave (AW) sensor for sensing the amount of a gas in a fluid flow, comprising:
a) a first gas-absorbing layer;
b) a high-temperature-stable piezoelectric plate coupled to the first gas-absorbing layer, the high-temperature-stable piezoelectric plate including at least one material selected from the group consisting of AlN, $Al_{1-x}Ga_xN$ (0<x≦1), $AlPO_4$, $Ca_2Ga_2Ge_4SiO_{14}$, $La_3Ga_5SiO_{14}$, $La_3Ga_{5.5}Nb_{0.5}O_{14}$, and $La_3Ga_{5.5}Ta_{0.5}O_{14}$, wherein the first gas-absorbing layer has a gas absorption/adsorption ratio of at least about 2000:1; and
c) a controller coupled to the high-temperature-stable piezoelectric plate to measure a resonant frequency in the high temperature stable piezoelectric plate correlated with an amount of gas absorbed by the first gas-absorbing layer,
whereby the amount of a gas in a fluid flow is sensed.

23. The AW sensor of claim 22, wherein the high-temperature-stable piezoelectric plate is stable as a single crystalline phase in an oxygen partial pressure range between about 5 atmospheres (atm) to about $10^{-22}$ atm and a temperature range between about −40° C. to 900° C.

24. The AW sensor of claim 23, wherein the high-temperature-stable piezoelectric plate is stable as a single crystalline phase in temperature range between about −30° C. to about 650° C.

25. The AW sensor of claim 23, wherein the high temperature stable piezoelectric plate consists essentially of $La_3Ga_5SiO_{14}$.

26. The AW sensor of claim 25, wherein the first gas-absorbing layer includes one or more materials selected from the group consisting of metal carbonates and zeolites.

27. The AW sensor of claim 26, wherein the AW sensor is in fluid communication with an exhaust stream from an external combustion process.

28. The AW sensor of claim 26, wherein the AW sensor is in fluid communication with a gas stream in a pyrolysis process.

29. The AW sensor of claim 26, wherein the AW sensor is in fluid communication with an exhaust stream from an internal combustion engine.

30. The AW sensor of claim 29, wherein the AW sensor is coupled with a gas trap, the trap including a second gas-absorbing layer.

31. The AW sensor of claim 30, wherein the first gas-absorbing layer includes barium carbonate.

32. The AW sensor of claim 31, wherein the AW sensor is in parallel with the gas trap.

33. The AW sensor of claim 31, wherein the AW sensor is in series with the gas trap, and the AW sensor is located upstream of the trap with respect to a flow direction of the exhaust stream.

34. The AW sensor of claim 31, wherein the AW sensor is in series with the gas trap, and the AW sensor is located downstream of the trap with respect to the flow direction of the exhaust stream.

35. The AW sensor of claim 34, wherein the controller is in electronic communication with the internal combustion engine to operate the engine in a lean burn mode or a rich burn mode in response to the amount of gas sensed in the exhaust stream by the AW sensor.

36. The AW sensor of claim 35, wherein the first gas-absorbing layer includes a zeolite selected from Linde Type A, zeolite beta, NaX, NaA, NaY, ZSM-5, H-ZSM-5, natrolite, chabazite, sodalite, faujasite, mordenite, MCM-41, MCM-48, and MCM-50.

37. The AW sensor of claim 36, wherein the controller is coupled to the first gas-absorbing layer to measure at least one electrical complex impedance value of the gas-absorbing layer that is correlated with the amount of gas absorbed by the first gas absorbing layer, whereby the amount of gas in the fluid flow is sensed.

38. The AW sensor of claim 37, wherein the controller compares the amount of gas sensed from both the frequency of the high temperature stable piezoelectric plate and the electrical complex impedance of the first gas absorbing layer.

39. The AW sensor of claim 38, wherein the zeolite has nanopore sizes between about 0.5 nm and about 0.6 nm.

40. The AW sensor of claim 39, wherein the controller is in electronic communication with a selective catalytic reduction (SCR) urea injection system coupled to the internal combustion engine.

41. An acoustic wave (AW) sensor for sensing the amount of a gas in a fluid flow, comprising:
a) a first gas-absorbing layer;
b) a high-temperature-stable piezoelectric plate coupled to the first gas-absorbing layer, the high-temperature-stable piezoelectric plate including at least one material selected from the group consisting of AlN, $Al_{1-x}Ga_xN$ ($0<x\leq1$), $AlPO_4$, $Ca_2Ga_2Ge_4SiO_{14}$, $La_3Ga_5SiO_{14}$, $La_3Ga_{5.5}Nb_{0.5}O_{14}$, and $La_3Ga_{5.5}Ta_{0.5}O_{14}$, wherein the first gas-absorbing layer has a surface area to volume ratio of less than about $1\times10^7$ cm$^2$:1 cm$^3$; and
c) a controller coupled to the high-temperature-stable piezoelectric plate to measure a resonant frequency in the high temperature stable piezoelectric plate correlated with an amount of gas absorbed by the first gas-absorbing layer.
whereby the amount of a gas in a fluid flow is sensed wherein the first gas-absorbing layer has a surface area to volume ratio of less than about $1\times10^7$ cm$^2$: 1 cm$^3$.

42. An acoustic wave (AW) sensor for sensing the amount of a gas in a fluid flow, comprising:
a) a first gas-absorbing layer;
b) a high-temperature-stable piezoelectric plate coupled to the first gas-absorbing layer, the high-temperature-stable piezoelectric plate including at least one material selected from the group consisting of AlN, $Al_{1-x}Ga_xN$ ($0<x\leq1$), $AlPO_4$, $Ca_2Ga_2Ge_4SiO_{14}$, $La_3Ga_5SiO_{14}$, $La_3Ga_{5.5}Nb_{0.5}O_{14}$, and $La_3Ga_{5.5}Ta_{0.5}O_{14}$, wherein the first gas-absorbing layer has an ordered microstructure of micropores between about 200 nm and about 1000 nm in diameter; and
c) a controller coupled to the high-temperature-stable piezoelectric plate to measure a resonant frequency in the high temperature stable piezoelectric plate correlated with an amount of gas absorbed by the first gas-absorbing layer,
whereby the amount of a gas in a fluid flow is sensed.

43. A method of sensing the amount of a gas component in a fluid flow, comprising the steps of:
a) operating an acoustic wave (AW) sensor at a first resonant frequency, the AW sensor including a piezoelectric plate coupled to a first gas-absorbing layer, the gas-absorbing layer comprising a metal carbonate, wherein the first gas-absorbing layer has a surface area to volume ratio of less than about $1\times10^7$ cm$^2$: 1 cm$^3$;
b) combining a fluid flow having a gas component with the first gas-absorbing layer; and
c) sensing at least one resonant frequency of the AW sensor,
whereby the resonant frequency can be correlated with the amount of gas absorbed in the first gas-absorbing layer, thereby sensing the amount of gas in the fluid flow.

44. A method of sensing the amount of a gas component in a fluid flow, comprising the steps of:
a) operating an acoustic wave (AW) sensor at a first resonant frequency, the AW sensor including a piezoelectric plate coupled to a first gas-absorbing layer, the gas-absorbing layer comprising a metal carbonate, wherein the piezoelectric plate is formed of one or more materials selected from the group consisting of AlN, GaN, $Al_{1-x}Ga_xN$ ($0\leq x\leq1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$, wherein the first gas-absorbing layer has a surface area to volume ratio of less than about $1\times10^7$ cm$^2$:1 $^3$;
b) combining a fluid flow having a gas component with the first gas-absorbing layer; and
c) sensing at least one resonant frequency of the AW sensor,
whereby the resonant frequency can be correlated with the amount of gas absorbed in the first gas-absorbing layer, thereby sensing the amount of gas in the fluid flow.

45. The method of claim 44, wherein the fluid flow is selected from the group consisting of an exhaust stream from an external combustion process, a gas stream in a pyrolysis process, and an exhaust stream from an internal combustion engine.

46. The method of claim 45, wherein the fluid flow is an exhaust stream from an internal combustion engine.

47. The method of claim 46, wherein the first gas-absorbing layer includes barium carbonate.

48. A method of sensing the amount of a gas component in a fluid flow, comprising the steps of:
   a) operating an acoustic wave (AW) sensor at a first resonant frequency, the AW sensor including a piezoelectric plate coupled to a first gas-absorbing layer, the gas-absorbing layer comprising a metal carbonate, wherein the piezoelectric plate is formed of one or more materials selected from the group consisting of AlN, GaN, $Al_{1-x}Ga_xN$ ($0 \leq x \leq 1$), $GaPO_4$, quartz, $LiNbO_3Li_2B_4O_7$, ZnO, lead zirconate titanate (PZT), $LiTaO_3$, and materials having the crystal structure of $Ca_2Ga_2Ge_4SiO_{14}$, and wherein the first gas-absorbing layer has a gas absorption/adsorption ratio of at least about 2000:1;
   b) combining a fluid flow having a gas component with the first gas-absorbing layer; and
   c) sensing at least one resonant frequency of the AW sensor,
whereby the resonant frequency can be correlated with the amount of gas absorbed in the first gas-absorbing layer, thereby sensing the amount of gas in the fluid flow.

49. A method of sensing the amount of a gas component in a fluid flow, comprising the steps of:
   a) operating an acoustic wave (AW) sensor at a first resonant frequency, the AW sensor including a piezoelectric plate coupled to a first gas-absorbing layer, the gas-absorbing layer comprising a metal carbonate, wherein the piezoelectric plate is formed of one or more materials selected from the group consisting of AlN, GaN, $Al_{1-x}Ga_xN$ ($0 \leq x \leq 1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$, wherein the first gas-absorbing layer has an ordered microstructure of micropores between about 200 nm and about 3000 nm in diameter;
   b) combining a fluid flow having a gas component with the first gas-absorbing layer; and
   c) sensing at least one resonant frequency of the AW sensor,
whereby the resonant frequency can be correlated with the amount of gas absorbed in the first gas-absorbing layer, thereby sensing the amount of gas in the fluid flow.

50. An acoustic wave (AW) sensor for sensing the amount of a gas in a fluid flow, comprising:
   a) a first gas-absorbing layer comprising a metal carbonate, wherein the first gas-absorbing layer has a surface area to volume ratio of less than about $1 \times 10^7$ $cm^2$: 1 $cm^3$;
   b) a piezoelectric plate coupled to the first gas-absorbing layer; and
   c) a controller coupled to the piezoelectric plate to measure a resonant frequency piezoelectric plate correlated with an amount of gas absorbed by the first gas-absorbing layer,
whereby the amount of a gas in a fluid flow is sensed.

51. An acoustic wave (AW) sensor for sensing the amount of a gas in a fluid flow, comprising:
   a) a first gas-absorbing layer comprising a metal carbonate, wherein the first gas-absorbing layer has a surface area to volume ratio of less than about $1 \times 10^7$ $cm^2$: 1 $cm^3$;
   b) a piezoelectric plate coupled to the first gas-absorbing layer, wherein the piezoelectric plate is formed of one or more materials selected from the group consisting of AlN, GaN, $Al_{1-x}Ga_xN$ ($0 \leq x \leq 1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$; and
   c) a controller coupled to the piezoelectric plate to measure a resonant frequency piezoelectric plate correlated with an amount of gas absorbed by the first gas-absorbing layer,
whereby the amount of a gas in a fluid flow is sensed.

52. The AW sensor of claim 51, wherein the AW sensor is coupled with a fluid flow selected from the group consisting of an exhaust stream from an external combustion process, a gas stream in a pyrolysis process, and an exhaust stream from an internal combustion engine.

53. The AW sensor of claim 52, wherein the fluid flow is an exhaust stream from an internal combustion engine.

54. The AW sensor of claim 53, wherein the first gas-absorbing layer includes barium carbonate.

55. An acoustic wave (AW) sensor for sensing the amount of a gas in a fluid flow, comprising:
   a) a first gas-absorbing layer comprising a metal carbonate, wherein the first gas-absorbing layer has a gas absorption/adsorption ratio of at least about 2000: 1;
   b) a piezoelectric plate coupled to the first gas-absorbing layer, wherein the piezoelectric plate is formed of one or more materials selected from the group consisting of AlN, GaN, $Al_{1-x}Ga_xN$ ($0 \leq x \leq 1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$; and
   c) a controller coupled to the piezoelectric plate to measure a resonant frequency piezoelectric plate correlated with an amount of gas absorbed by the first gas-absorbing layer,
whereby the amount of a gas in a fluid flow is sensed.

56. An acoustic wave (AW) sensor for sensing the amount of a gas in a fluid flow, comprising:
   a) a first gas-absorbing layer comprising a metal carbonate, wherein the first gas-absorbing layer has an ordered microstructure of micropores between about 200 nm and about 3000 nm in diameters,
   b) a piezoelectric elate coupled to the first gas-absorbing layer, wherein the piezoelectric plate is formed of one or more materials selected from the group consisting of AlN, GaN, $Al_{1-x}Ga_xN$ ($0 \leq x \leq 1$), $GaPO_4$, $AlPO_4$, quartz, $LiNbO_3$, $Li_2B_4O_7$, ZnO, lead zirconate titanate (PZT), $LiTaO_3$, and materials having the crystal structure of $Ca_2Ga_2Ge_4SiO_{14}$; and
   c) a controller coupled to the piezoelectric plate to measure a resonant frequency piezoelectric plate correlated with an amount of gas absorbed by the first gas-absorbing layer,
whereby the amount of a gas in a fluid flow is sensed.

57. A method of sensing the amount of a gas component in a fluid flow, comprising the steps of:
   a) operating an acoustic wave (AW) sensor at a first resonant frequency, the AW sensor including a piezoelectric plate coupled to a first gas-absorbing layer, the gas-absorbing layer including a metal carbonate or a zeolite;
   b) combining a fluid flow having a gas component with the first gas-absorbing layer;
   c) sensing at least one resonant frequency of the AW sensor; and
   d) sensing at least one electrical complex impedance value of the gas-absorbing layer, whereby the resonant frequency can be correlated with the amount of gas absorbed in the first gas-absorbing layer, and the electrical complex impedance value of the gas-absorbing layer can be correlated with the amount of gas absorbed by the first gas absorbing layer, thereby sensing the amount of gas in the fluid flow.

58. An acoustic wave (AW) sensor for sensing the amount of a gas in a fluid flow, comprising:
  a) a first gas-absorbing layer including a metal carbonate or a zeolite;
  b) a piezoelectric plate coupled to the first gas-absorbing layer; and
  c) a controller;
    i) coupled to the piezoelectric plate to measure a resonant frequency correlated with an amount of gas absorbed by the first gas absorbing layer; and
    ii) coupled to the gas absorbing layer to measure an electrical complex impedance value correlated with an amount of gas absorbed by the first gas-absorbing layer,
whereby the amount of a gas in a fluid flow is sensed.

* * * * *

UNITED STATES PATENT AND TRADEMARK OFFICE
CERTIFICATE OF CORRECTION

PATENT NO. : 7,194,891 B2  
APPLICATION NO. : 10/828096  
DATED : March 27, 2007  
INVENTOR(S) : Harry L. Tuller, Huankiat Seh and Takeo Hyodo It is certified that error appears in the above-identified patent and that said Letters Patent is hereby corrected as shown below:

In Claim 19, Column 17, line 36, "elate" should be --plate--;

In Claim 22, Column 18, line 36, "$La_3Ga_xSiO_{14}$" should be -- $La_3Ga_5SiO_{14}$--;

In Claim 48, Column 21, line 9, before "quartz" should be --$AlPO_4$,--;

In Claim 56, Column 22, line 42, "elate" should be --plate--.

Signed and Sealed this

Fourteenth Day of August, 2007

JON W. DUDAS  
*Director of the United States Patent and Trademark Office*